US008758391B2

(12) United States Patent
Swayze et al.

(10) Patent No.: US 8,758,391 B2
(45) Date of Patent: Jun. 24, 2014

(54) INTERCHANGEABLE TOOLS FOR SURGICAL INSTRUMENTS

(75) Inventors: Jeffrey S. Swayze, Hamilton, OH (US); Thomas W. Huitema, Cincinnati, OH (US); Glen A. Armstrong, Hamilton, OH (US); Shailendra K. Parihar, Mason, OH (US); Donna L. Korvick, Maineville, OH (US); Richard W. Timm, Cincinnati, OH (US); Frederick E. Shelton, IV, Hillsboro, OH (US); Kevin R. Doll, Mason, OH (US); Bret W. Smith, Kings Mills, OH (US); William D. Kelly, Mason, OH (US); Ronald J. Kolata, Raleigh, NC (US); Joshua R. Uth, Mason, OH (US); Charles J. Scheib, Loveland, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1174 days.

(21) Appl. No.: 12/031,611

(22) Filed: Feb. 14, 2008

(65) Prior Publication Data
US 2009/0209946 A1    Aug. 20, 2009

(51) Int. Cl.
A61B 17/00    (2006.01)
(52) U.S. Cl.
USPC .......................................................... 606/205
(58) Field of Classification Search
USPC ............... 606/174, 207, 206, 205, 51, 46, 52; 227/175.1, 177.1, 181.1, 175.2, 175.3, 227/19
See application file for complete search history.

(56) References Cited

U.S. PATENT DOCUMENTS

| 2,804,848 A | 9/1957 | O'Farrell et al. |
| 2,853,074 A | 9/1958 | Olson |

(Continued)

FOREIGN PATENT DOCUMENTS

| CA | 2458946 A1 | 3/2003 |
| CA | 2512960 A1 | 1/2006 |

(Continued)

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

(Continued)

*Primary Examiner* — Tuan V Nguyen
*Assistant Examiner* — Tin Nguyen

(57) ABSTRACT

A surgical tool system. Various embodiments of the surgical tool system may comprise surgical instrument that has a handle assembly that operably supports a drive system therein for generating drive motions upon actuation of a movable handle portion operably coupled to the handle assembly. An elongated body protrudes from the handle assembly and operably supports a control rod therein that interfaces with the drive system. The surgical tool system further includes at least two surgical tools selected from the group of surgical tools consisting of: manipulators, nippers, scissors, endocutters, tissue thickness measurement devices, staple appliers, clip appliers, syringes for applying glue, sealant, drugs or medicaments and cauterization devices wherein each of the surgical tool within the group of surgical tools at least has a housing that is removably couplable to the elongated body and a drive assembly that is removably couplable to the control rod for receiving the drive motions therefrom.

16 Claims, 28 Drawing Sheets

(56) References Cited

U.S. PATENT DOCUMENTS

| | | | |
|---|---|---|---|
| 3,266,494 | A | 8/1966 | Brownrigg et al. |
| 3,490,675 | A | 1/1970 | Green et al. |
| 3,551,987 | A | 1/1971 | Wilkinson |
| 3,643,851 | A | 2/1972 | Green et al. |
| 3,662,939 | A | 5/1972 | Bryan |
| 3,717,294 | A | 2/1973 | Green |
| 3,819,100 | A | 6/1974 | Noiles et al. |
| 4,331,277 | A | 5/1982 | Green |
| 4,383,634 | A | 5/1983 | Green |
| 4,396,139 | A | 8/1983 | Hall et al. |
| 4,402,445 | A | 9/1983 | Green |
| 4,415,112 | A | 11/1983 | Green |
| 4,429,695 | A | 2/1984 | Green |
| 4,475,679 | A | 10/1984 | Fleury, Jr. |
| 4,489,875 | A | 12/1984 | Crawford et al. |
| 4,500,024 | A | 2/1985 | DiGiovanni et al. |
| 4,505,273 | A | 3/1985 | Braun et al. |
| 4,505,414 | A | 3/1985 | Filipi |
| 4,506,671 | A | 3/1985 | Green |
| 4,522,327 | A | 6/1985 | Korthoff et al. |
| 4,530,453 | A | 7/1985 | Green |
| 4,566,620 | A | 1/1986 | Green et al. |
| 4,573,622 | A | 3/1986 | Green et al. |
| 4,576,167 | A | 3/1986 | Noiles et al. |
| 4,580,712 | A | 4/1986 | Green |
| 4,610,250 | A | 9/1986 | Green |
| 4,610,383 | A | 9/1986 | Rothfuss et al. |
| 4,619,262 | A | 10/1986 | Taylor |
| 4,629,107 | A | 12/1986 | Fedotov et al. |
| 4,655,222 | A | 4/1987 | Florez et al. |
| 4,664,305 | A | 5/1987 | Blake, III et al. |
| 4,667,674 | A | 5/1987 | Korthoff et al. |
| 4,671,445 | A | 6/1987 | Barker et al. |
| 4,715,520 | A | 12/1987 | Roehr, Jr. et al. |
| 4,728,020 | A | 3/1988 | Green et al. |
| 4,752,024 | A | 6/1988 | Green et al. |
| 4,754,909 | A | 7/1988 | Barker et al. |
| 4,767,044 | A | 8/1988 | Green |
| 4,790,225 | A | 12/1988 | Moody et al. |
| 4,805,823 | A | 2/1989 | Rothfuss |
| 4,809,695 | A | 3/1989 | Gwathmey et al. |
| 4,817,847 | A | 4/1989 | Redtenbacher et al. |
| 4,819,853 | A | 4/1989 | Green |
| 4,821,939 | A | 4/1989 | Green |
| 4,844,068 | A | 7/1989 | Arata et al. |
| 4,869,414 | A | 9/1989 | Green et al. |
| 4,869,415 | A | 9/1989 | Fox |
| 4,880,015 | A | 11/1989 | Nierman |
| 4,941,623 | A | 7/1990 | Pruitt |
| 4,944,443 | A | 7/1990 | Oddsen et al. |
| 5,014,899 | A | 5/1991 | Presty et al. |
| 5,042,707 | A | 8/1991 | Taheri |
| 5,065,929 | A | 11/1991 | Schulze et al. |
| 5,071,430 | A | 12/1991 | de Salis et al. |
| 5,084,057 | A | 1/1992 | Green et al. |
| 5,116,349 | A | 5/1992 | Aranyi |
| 5,129,570 | A | 7/1992 | Schulze et al. |
| 5,137,198 | A | 8/1992 | Nobis et al. |
| 5,139,513 | A | 8/1992 | Segato |
| 5,158,567 | A | 10/1992 | Green |
| 5,171,247 | A | 12/1992 | Hughett et al. |
| 5,171,249 | A | 12/1992 | Stefanchik et al. |
| 5,209,747 | A | 5/1993 | Knoepfler |
| 5,211,649 | A | 5/1993 | Kohler et al. |
| 5,221,036 | A | 6/1993 | Takase |
| 5,222,975 | A | 6/1993 | Crainich |
| 5,236,440 | A | 8/1993 | Hlavacek |
| 5,246,443 | A | 9/1993 | Mai |
| 5,258,009 | A | 11/1993 | Conners |
| 5,282,806 | A | 2/1994 | Haber et al. |
| 5,282,829 | A | 2/1994 | Hermes |
| 5,304,204 | A | 4/1994 | Bregen |
| 5,314,424 | A | 5/1994 | Nicholas |
| 5,330,502 | A | 7/1994 | Hassler et al. |
| 5,333,422 | A | 8/1994 | Warren et al. |
| 5,341,724 | A | 8/1994 | Vatel |
| 5,342,395 | A | 8/1994 | Jarrett et al. |
| 5,342,396 | A | 8/1994 | Cook |
| 5,350,400 | A | 9/1994 | Esposito et al. |
| 5,352,235 | A | 10/1994 | Koros et al. |
| 5,352,238 | A | 10/1994 | Green et al. |
| 5,354,303 | A * | 10/1994 | Spaeth et al. .............. 606/128 |
| 5,358,510 | A | 10/1994 | Luscombe et al. |
| 5,366,479 | A | 11/1994 | McGarry et al. |
| 5,374,277 | A | 12/1994 | Hassler |
| 5,379,933 | A | 1/1995 | Green et al. |
| 5,383,880 | A | 1/1995 | Hooven |
| 5,383,888 | A | 1/1995 | Zvenyatsky et al. |
| 5,383,895 | A | 1/1995 | Holmes et al. |
| 5,389,098 | A | 2/1995 | Tsuruta et al. |
| 5,391,180 | A | 2/1995 | Tovey et al. |
| 5,397,324 | A | 3/1995 | Carroll et al. |
| 5,405,072 | A | 4/1995 | Zlock et al. |
| 5,405,344 | A | 4/1995 | Williamson et al. |
| 5,413,272 | A | 5/1995 | Green et al. |
| 5,415,334 | A | 5/1995 | Williamson, IV et al. |
| 5,417,361 | A | 5/1995 | Williamson, IV |
| 5,425,745 | A | 6/1995 | Green et al. |
| 5,441,494 | A | 8/1995 | Ortiz |
| 5,449,365 | A | 9/1995 | Green et al. |
| 5,456,401 | A | 10/1995 | Green et al. |
| 5,474,566 | A | 12/1995 | Alesi et al. |
| 5,476,479 | A | 12/1995 | Green et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,487,499 | A | 1/1996 | Sorrentino et al. |
| 5,487,500 | A | 1/1996 | Knodel et al. |
| 5,489,058 | A | 2/1996 | Plyley et al. |
| 5,497,933 | A | 3/1996 | DeFonzo et al. |
| 5,503,320 | A | 4/1996 | Webster et al. |
| 5,503,638 | A | 4/1996 | Cooper et al. |
| 5,505,363 | A | 4/1996 | Green et al. |
| 5,509,596 | A | 4/1996 | Green et al. |
| 5,514,157 | A | 5/1996 | Nicholas et al. |
| 5,520,700 | A | 5/1996 | Beyar et al. |
| 5,529,235 | A | 6/1996 | Boiarski et al. |
| 5,533,521 | A * | 7/1996 | Granger ..................... 600/587 |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,542,594 | A | 8/1996 | McKean et al. |
| 5,547,117 | A | 8/1996 | Hamblin et al. |
| 5,549,628 | A | 8/1996 | Cooper et al. |
| 5,549,637 | A | 8/1996 | Crainich |
| 5,553,765 | A | 9/1996 | Knodel et al. |
| 5,554,169 | A | 9/1996 | Green et al. |
| 5,558,665 | A | 9/1996 | Kieturakis |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,702 | A | 10/1996 | Huitema et al. |
| 5,564,615 | A | 10/1996 | Bishop et al. |
| 5,569,284 | A | 10/1996 | Young et al. |
| 5,571,116 | A | 11/1996 | Bolanos et al. |
| 5,575,799 | A | 11/1996 | Bolanos et al. |
| 5,575,803 | A | 11/1996 | Cooper et al. |
| 5,577,654 | A | 11/1996 | Bishop |
| 5,579,978 | A | 12/1996 | Green et al. |
| 5,580,067 | A | 12/1996 | Hamblin et al. |
| 5,582,611 | A | 12/1996 | Tsuruta et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |

(56) References Cited

U.S. PATENT DOCUMENTS

| | | | |
|---|---|---|---|
| 5,597,107 A | 1/1997 | Knodel et al. | |
| 5,601,224 A * | 2/1997 | Bishop et al. | 227/175.1 |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,607,450 A | 3/1997 | Zvenyatsky et al. | |
| 5,609,285 A | 3/1997 | Grant et al. | |
| 5,618,303 A | 4/1997 | Marlow et al. | |
| 5,624,452 A | 4/1997 | Yates | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |
| 5,636,779 A | 6/1997 | Palmer | |
| 5,636,780 A | 6/1997 | Green et al. | |
| 5,639,008 A | 6/1997 | Gallagher et al. | |
| 5,645,209 A | 7/1997 | Green et al. | |
| 5,647,526 A | 7/1997 | Green et al. | |
| 5,649,937 A | 7/1997 | Bito et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,260 A | 9/1997 | Yoon | |
| 5,667,527 A | 9/1997 | Cook | |
| 5,669,544 A | 9/1997 | Schulze et al. | |
| 5,669,918 A | 9/1997 | Balazs et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,685,474 A | 11/1997 | Seeber | |
| 5,688,270 A | 11/1997 | Yates et al. | |
| 5,690,269 A | 11/1997 | Bolanos et al. | |
| 5,692,668 A | 12/1997 | Schulze et al. | |
| 5,697,543 A | 12/1997 | Burdorff | |
| 5,700,270 A | 12/1997 | Peyser et al. | |
| 5,702,408 A | 12/1997 | Wales et al. | |
| 5,704,534 A | 1/1998 | Huitema et al. | |
| 5,706,997 A | 1/1998 | Green et al. | |
| 5,706,998 A | 1/1998 | Plyley et al. | |
| 5,707,392 A | 1/1998 | Kortenbach | |
| 5,709,334 A | 1/1998 | Sorrentino et al. | |
| 5,709,706 A | 1/1998 | Kienzle et al. | |
| 5,711,472 A | 1/1998 | Bryan | |
| 5,713,505 A | 2/1998 | Huitema | |
| 5,713,896 A | 2/1998 | Nardella | |
| 5,715,987 A | 2/1998 | Kelley et al. | |
| 5,715,988 A | 2/1998 | Palmer | |
| 5,716,366 A | 2/1998 | Yates | |
| 5,718,359 A | 2/1998 | Palmer et al. | |
| 5,718,360 A | 2/1998 | Green et al. | |
| 5,725,536 A | 3/1998 | Oberlin et al. | |
| 5,725,554 A | 3/1998 | Simon et al. | |
| 5,728,121 A | 3/1998 | Bimbo et al. | |
| 5,730,758 A | 3/1998 | Allgeyer | |
| 5,732,871 A | 3/1998 | Clark et al. | |
| 5,732,872 A | 3/1998 | Bolduc et al. | |
| 5,735,445 A | 4/1998 | Vidal et al. | |
| 5,735,874 A | 4/1998 | Measamer et al. | |
| 5,743,456 A | 4/1998 | Jones et al. | |
| 5,749,893 A | 5/1998 | Vidal et al. | |
| 5,752,644 A | 5/1998 | Bolanos et al. | |
| 5,758,814 A | 6/1998 | Gallagher et al. | |
| 5,762,255 A | 6/1998 | Chrisman et al. | |
| 5,762,256 A | 6/1998 | Mastri et al. | |
| 5,766,205 A | 6/1998 | Zvenyatsky et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,782,859 A | 7/1998 | Nicholas et al. | |
| 5,785,232 A | 7/1998 | Vidal et al. | |
| 5,794,834 A | 8/1998 | Hamblin et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,797,959 A | 8/1998 | Castro et al. | |
| 5,799,857 A | 9/1998 | Robertson et al. | |
| 5,807,376 A | 9/1998 | Viola et al. | |
| 5,807,393 A | 9/1998 | Williamson, IV et al. | |
| 5,817,119 A | 10/1998 | Klieman et al. | |
| 5,820,009 A | 10/1998 | Melling et al. | |
| 5,826,776 A | 10/1998 | Schulze et al. | |
| 5,829,662 A * | 11/1998 | Allen et al. | 227/177.1 |
| 5,833,690 A | 11/1998 | Yates et al. | |
| 5,833,695 A | 11/1998 | Yoon | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,868,760 A | 2/1999 | McGuckin, Jr. | |
| 5,871,135 A | 2/1999 | Williamson, IV et al. | |
| 5,876,401 A | 3/1999 | Schulze et al. | |
| 5,878,937 A | 3/1999 | Green et al. | |
| 5,878,938 A | 3/1999 | Bittner et al. | |
| 5,893,506 A | 4/1999 | Powell | |
| 5,894,979 A | 4/1999 | Powell | |
| 5,897,562 A | 4/1999 | Bolanos et al. | |
| 5,901,895 A | 5/1999 | Heaton et al. | |
| 5,906,625 A | 5/1999 | Bito et al. | |
| 5,908,427 A | 6/1999 | McKean et al. | |
| 5,911,353 A | 6/1999 | Bolanos et al. | |
| 5,915,616 A | 6/1999 | Viola et al. | |
| 5,918,791 A | 7/1999 | Sorrentino et al. | |
| 5,919,198 A | 7/1999 | Graves, Jr. et al. | |
| 5,938,667 A | 8/1999 | Peyser et al. | |
| 5,941,442 A | 8/1999 | Geiste et al. | |
| 5,951,552 A | 9/1999 | Long et al. | |
| 5,951,574 A | 9/1999 | Stefanchik et al. | |
| 5,954,259 A | 9/1999 | Viola et al. | |
| 5,988,479 A | 11/1999 | Palmer | |
| 6,010,054 A | 1/2000 | Johnson et al. | |
| 6,024,741 A | 2/2000 | Williamson, IV et al. | |
| 6,032,849 A | 3/2000 | Mastri et al. | |
| 6,033,427 A | 3/2000 | Lee | |
| 6,045,560 A | 4/2000 | McKean et al. | |
| 6,050,472 A | 4/2000 | Shibata | |
| 6,079,606 A | 6/2000 | Milliman et al. | |
| 6,083,242 A | 7/2000 | Cook | |
| 6,086,600 A | 7/2000 | Kortenbach | |
| 6,099,551 A | 8/2000 | Gabbay | |
| 6,102,271 A | 8/2000 | Longo et al. | |
| 6,109,500 A | 8/2000 | Alli et al. | |
| 6,117,158 A | 9/2000 | Measamer et al. | |
| 6,119,913 A | 9/2000 | Adams et al. | |
| 6,126,058 A | 10/2000 | Adams et al. | |
| 6,131,789 A | 10/2000 | Schulze et al. | |
| 6,155,473 A | 12/2000 | Tompkins et al. | |
| 6,156,056 A | 12/2000 | Kearns et al. | |
| 6,162,208 A | 12/2000 | Hipps | |
| 6,168,605 B1 | 1/2001 | Measamer et al. | |
| 6,171,330 B1 | 1/2001 | Benchetrit | |
| 6,197,042 B1 | 3/2001 | Ginn et al. | |
| 6,202,914 B1 | 3/2001 | Geiste et al. | |
| 6,214,028 B1 | 4/2001 | Yoon et al. | |
| 6,228,084 B1 | 5/2001 | Kirwan, Jr. | |
| 6,241,139 B1 | 6/2001 | Milliman et al. | |
| 6,241,723 B1 | 6/2001 | Heim et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,273,897 B1 | 8/2001 | Dalessandro et al. | |

(56) References Cited

U.S. PATENT DOCUMENTS

| | | |
|---|---|---|
| 6,302,311 B1 | 10/2001 | Adams et al. |
| 6,309,403 B1 | 10/2001 | Minor et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,387,113 B1 | 5/2002 | Hawkins et al. |
| 6,387,114 B2 | 5/2002 | Adams |
| 6,406,440 B1 | 6/2002 | Stefanchik |
| RE37,814 E | 8/2002 | Allgeyer |
| 6,436,107 B1 | 8/2002 | Wang et al. |
| 6,443,973 B1 | 9/2002 | Whitman |
| 6,482,200 B2 | 11/2002 | Shippert |
| 6,488,196 B1 | 12/2002 | Fenton, Jr. |
| 6,488,197 B1 | 12/2002 | Whitman |
| 6,491,201 B1 | 12/2002 | Whitman |
| 6,494,896 B1 | 12/2002 | D'Alessio et al. |
| 6,503,257 B2 | 1/2003 | Grant et al. |
| 6,505,768 B2 | 1/2003 | Whitman |
| 6,517,565 B1 | 2/2003 | Whitman et al. |
| 6,569,171 B2 | 5/2003 | DeGuillebon et al. |
| 6,578,751 B2 | 6/2003 | Hartwick |
| 6,588,643 B2 | 7/2003 | Bolduc et al. |
| 6,592,597 B2 | 7/2003 | Grant et al. |
| 6,601,749 B2 | 8/2003 | Sullivan et al. |
| 6,602,252 B2 | 8/2003 | Mollenauer |
| 6,605,078 B2 | 8/2003 | Adams |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,685,727 B2 | 2/2004 | Fisher et al. |
| 6,695,199 B2 | 2/2004 | Whitman |
| 6,698,643 B2 | 3/2004 | Whitman |
| 6,712,773 B1 | 3/2004 | Viola |
| 6,716,232 B1 | 4/2004 | Vidal et al. |
| 6,716,233 B1 | 4/2004 | Whitman |
| 6,723,087 B2 | 4/2004 | O'Neill et al. |
| 6,752,768 B2 | 6/2004 | Burdorff et al. |
| 6,755,338 B2 | 6/2004 | Hahnen et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,786,382 B1 | 9/2004 | Hoffman |
| 6,786,896 B1 | 9/2004 | Madani et al. |
| 6,793,652 B1 | 9/2004 | Whitman et al. |
| 6,805,273 B2 | 10/2004 | Bilotti et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,821,273 B2 | 11/2004 | Mollenauer |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,913,613 B2 | 7/2005 | Schwarz et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,087,071 B2 | 8/2006 | Nicholas et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,108,695 B2 | 9/2006 | Witt et al. |
| 7,108,709 B2 | 9/2006 | Cummins |
| 7,111,769 B2 | 9/2006 | Wales et al. |
| 7,112,214 B2 | 9/2006 | Peterson et al. |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,650 B2 | 12/2006 | Lee |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,188,758 B2 | 3/2007 | Viola et al. |
| 7,189,207 B2 | 3/2007 | Viola |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et |
| 7,213,736 B2 | 5/2007 | Wales et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,328,828 B2 | 2/2008 | Ortiz et al. |
| 7,328,829 B2 | 2/2008 | Arad et al. |
| 7,338,513 B2 | 3/2008 | Lee et al. |

(56) References Cited

U.S. PATENT DOCUMENTS

| | | | |
|---|---|---|---|
| 7,343,920 B2 | 3/2008 | Toby et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,481,824 B2 | 1/2009 | Boudreaux et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,559,450 B2 | 7/2009 | Wales et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,631,793 B2 | 12/2009 | Rethy et al. |
| 7,641,093 B2 | 1/2010 | Doll et al. |
| 7,651,017 B2 | 1/2010 | Ortiz et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 7,674,255 B2 | 3/2010 | Braun |
| 7,686,826 B2 | 3/2010 | Lee et al. |
| 7,717,312 B2 | 5/2010 | Beetel |
| 7,731,072 B2 | 6/2010 | Timm et al. |
| 7,735,703 B2 | 6/2010 | Morgan et al. |
| 7,743,960 B2 | 6/2010 | Whitman et al. |
| 7,753,245 B2 | 7/2010 | Boudreaux et al. |
| 7,766,209 B2 | 8/2010 | Baxter, III et al. |
| 7,780,054 B2 | 8/2010 | Wales |
| 7,784,662 B2 | 8/2010 | Wales et al. |
| 7,793,812 B2 | 9/2010 | Moore et al. |
| 7,798,386 B2 | 9/2010 | Schall et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,837,080 B2 | 11/2010 | Schwemberger |
| 7,845,534 B2 | 12/2010 | Viola et al. |
| 7,870,989 B2 | 1/2011 | Viola et al. |
| 8,011,551 B2 | 9/2011 | Marczyk et al. |
| 8,540,130 B2 | 9/2013 | Moore et al. |
| 8,573,465 B2 | 11/2013 | Shelton, IV et al. |
| 2002/0117534 A1 | 8/2002 | Green et al. |
| 2002/0165541 A1 | 11/2002 | Whitman |
| 2004/0006372 A1 | 1/2004 | Racenet et al. |
| 2004/0034369 A1 | 2/2004 | Sauer et al. |
| 2004/0044364 A1 | 3/2004 | DeVries et al. |
| 2004/0094597 A1 | 5/2004 | Whitman et al. |
| 2004/0108357 A1* | 6/2004 | Milliman et al. ......... 227/176.1 |
| 2004/0111081 A1 | 6/2004 | Whitman et al. |
| 2004/0122423 A1* | 6/2004 | Dycus et al. .................... 606/51 |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0080454 A1 | 4/2005 | Drews et al. |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0131457 A1 | 6/2005 | Douglas et al. |
| 2005/0143759 A1 | 6/2005 | Kelly |
| 2005/0171522 A1 | 8/2005 | Christopherson |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0256522 A1 | 11/2005 | Francischelli et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085031 A1 | 4/2006 | Bettuchi |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0149163 A1 | 7/2006 | Hibner et al. |
| 2006/0151567 A1 | 7/2006 | Roy |
| 2006/0180634 A1 | 8/2006 | Shelton, IV et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0259073 A1 | 11/2006 | Miyamoto et al. |
| 2006/0273135 A1* | 12/2006 | Beetel ......................... 227/175.1 |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |

(56) References Cited

U.S. PATENT DOCUMENTS

| | | |
|---|---|---|
| 2007/0027469 A1* | 2/2007 | Smith et al. .................. 606/205 |
| 2007/0034668 A1 | 2/2007 | Holsten et al. |
| 2007/0045379 A1 | 3/2007 | Shelton, IV |
| 2007/0055219 A1 | 3/2007 | Whitman et al. |
| 2007/0073340 A1 | 3/2007 | Shelton, IV et al. |
| 2007/0073341 A1 | 3/2007 | Smith et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0288044 A1 | 12/2007 | Jinno et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0296347 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2010/0001036 A1 | 1/2010 | Marczyk et al. |
| 2010/0032470 A1 | 2/2010 | Hess et al. |
| 2010/0049084 A1 | 2/2010 | Nock et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |

(56) References Cited

U.S. PATENT DOCUMENTS

| | | |
|---|---|---|
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125177 A1 | 5/2011 | Yates et al. |
| 2011/0290855 A1 | 12/2011 | Moore et al. |
| 2013/0200132 A1 | 8/2013 | Moore et al. |

FOREIGN PATENT DOCUMENTS

| | | |
|---|---|---|
| CA | 2514274 A1 | 1/2006 |
| DE | 273689 C | 5/1914 |
| DE | 1775926 A | 1/1972 |
| DE | 3210466 A1 | 9/1983 |
| DE | 9412228 U | 9/1994 |
| DE | 19509116 A1 | 9/1996 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0748614 A1 | 12/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0598618 B1 | 9/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 1284120 A1 | 2/2003 |
| EP | 0829235 B1 | 6/2003 |
| EP | 0813843 B1 | 10/2003 |
| EP | 0741996 B1 | 2/2004 |
| EP | 1402837 A1 | 3/2004 |
| EP | 0705570 B1 | 4/2004 |
| EP | 1086713 B1 | 5/2004 |
| EP | 1426012 A1 | 6/2004 |
| EP | 1442694 A1 | 8/2004 |
| EP | 0888749 B1 | 9/2004 |
| EP | 1459695 A1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1157666 B1 | 9/2005 |
| EP | 0880338 B1 | 10/2005 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1256317 B1 | 12/2006 |
| EP | 1728473 A1 | 12/2006 |
| EP | 1728475 A2 | 12/2006 |

(56) References Cited

FOREIGN PATENT DOCUMENTS

| | | |
|---|---|---|
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1702568 B1 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 1759640 B1 | 12/2008 |
| EP | 2000102 A2 | 12/2008 |
| EP | 1749486 B1 | 3/2009 |
| EP | 2090256 A2 | 8/2009 |
| EP | 1607050 B1 | 12/2009 |
| EP | 1878395 B1 | 1/2010 |
| EP | 1566150 B1 | 4/2010 |
| EP | 1813206 B1 | 4/2010 |
| EP | 1769754 B1 | 6/2010 |
| EP | 1535565 81 | 10/2010 |
| EP | 1702570 B1 | 10/2010 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 2109241 A | 6/1983 |
| GB | 2272159 A | 5/1994 |
| GB | 2284242 A | 5/1995 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | H 09-164144 (A) | 6/1997 |
| JP | H 10-118090 (A) | 5/1998 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001286477 A | 10/2001 |
| JP | 2002143078 A | 5/2002 |
| JP | 2002369820 A | 12/2002 |
| JP | 2004-532676 (A) | 10/2004 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 93/14690 A1 | 8/1993 |
| WO | WO 94/11057 A1 | 5/1994 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/01080 A1 | 1/1998 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/48506 A1 | 8/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A2 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/086987 A1 | 10/2004 |

(56) References Cited

FOREIGN PATENT DOCUMENTS

| WO | WO 2004/096015 A2 | 11/2004 |
|---|---|---|
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

U.S. Appl. No. 12/031,001, filed Feb. 14, 2008.
U.S. Appl. No. 12/031,628, filed Feb. 14, 2008.
U.S. Appl. No. 11/729,008, filed Mar. 28, 2007.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
U.S. Appl. No. 11/821,277, filed Jun. 22, 2007.
U.S. Appl. No. 12/031,368, filed Feb. 14, 2008.
U.S. Appl. No. 12/031,326, filed Feb. 14, 2008.
U.S. Appl. No. 12/030,980, filed Feb. 14, 2008.
U.S. Appl. No. 12/031,066, filed Feb. 14, 2008.
U.S. Appl. No. 12/031,030, filed Feb. 14, 2008.
U.S. Appl. No. 12/030,974, filed Feb. 14, 2008.
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
European Search Report for Application No. 09250375.4, dated May 27, 2013 (18 pages).

\* cited by examiner

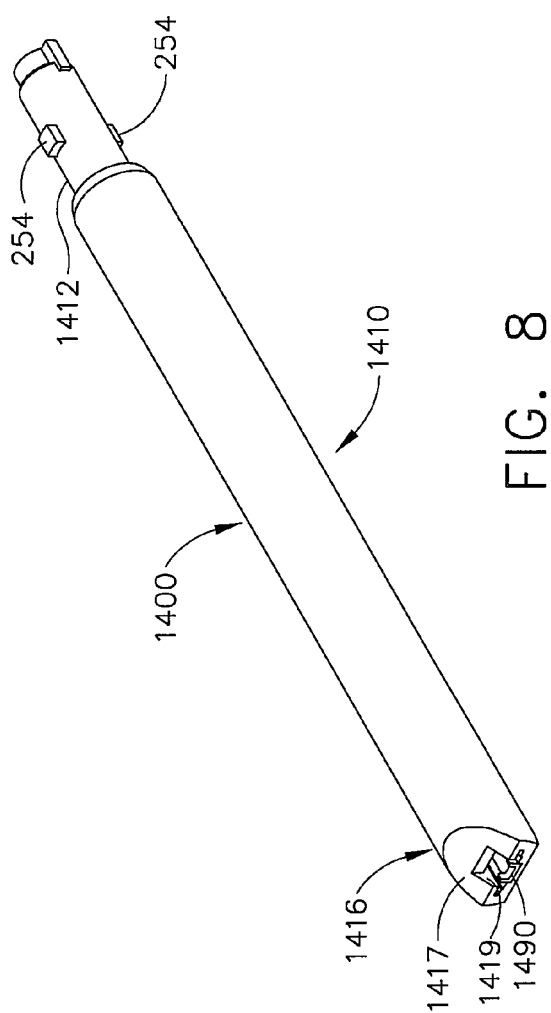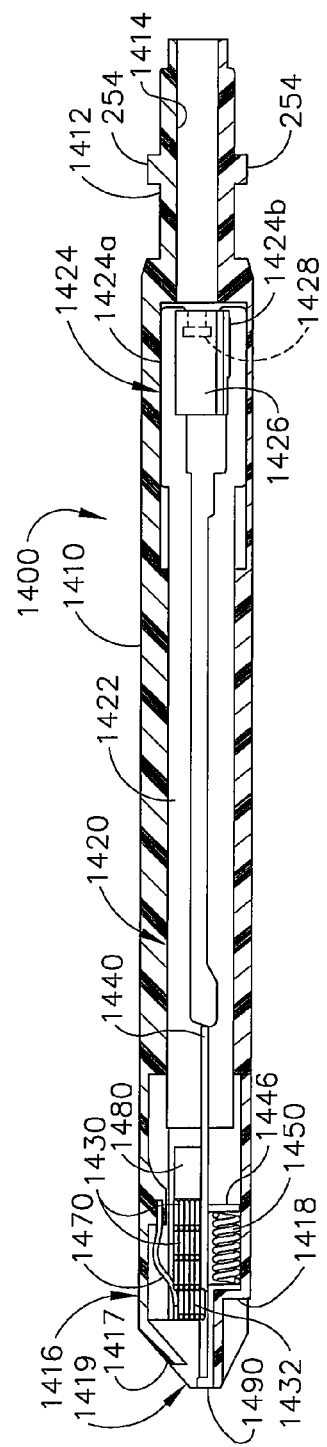

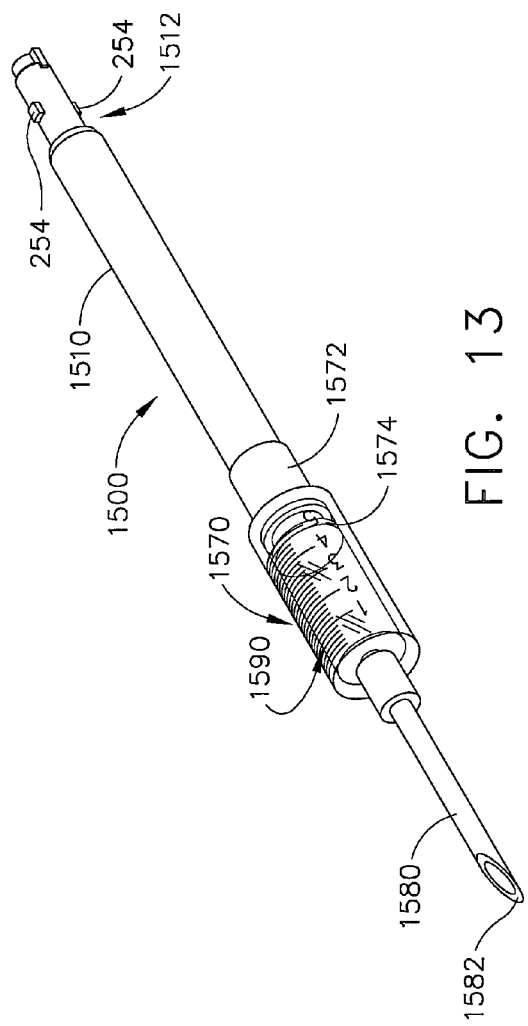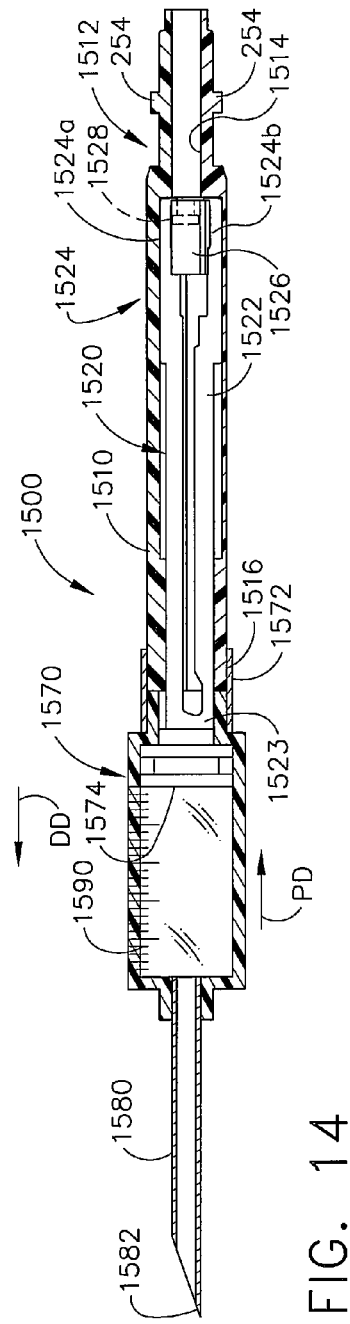

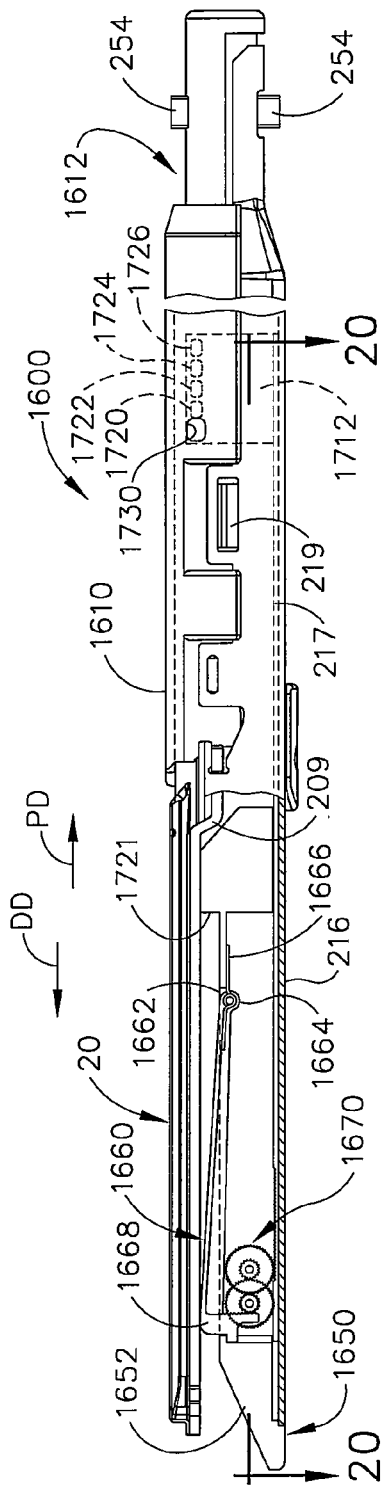

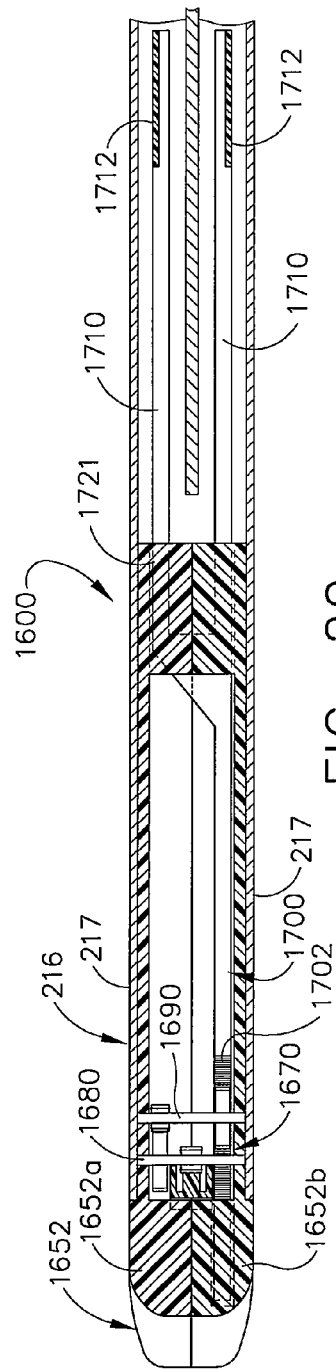
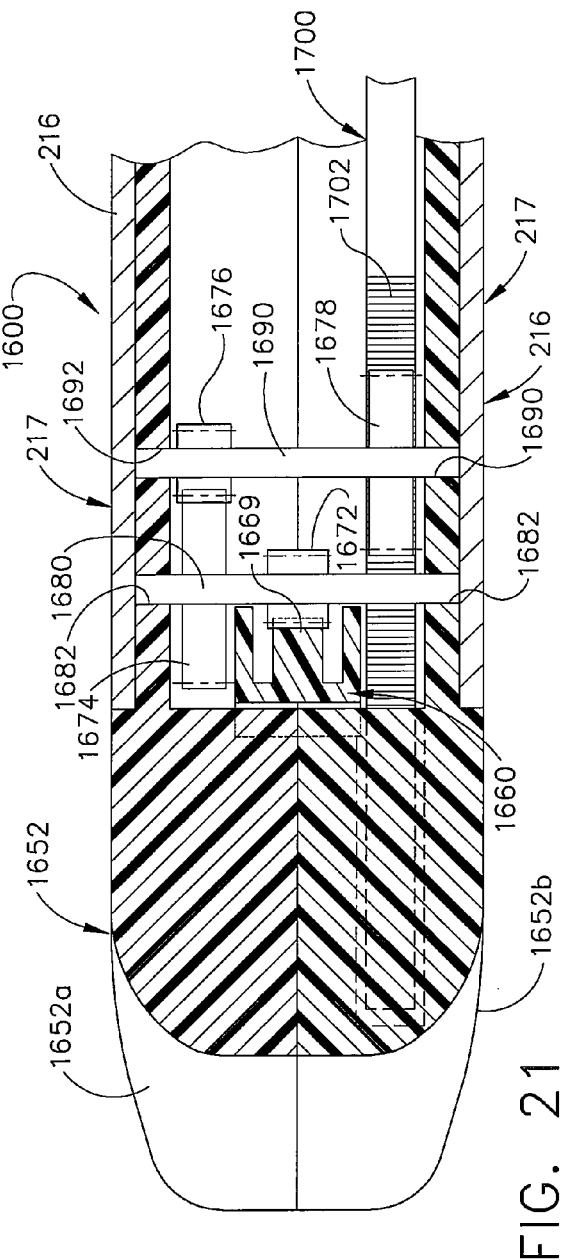

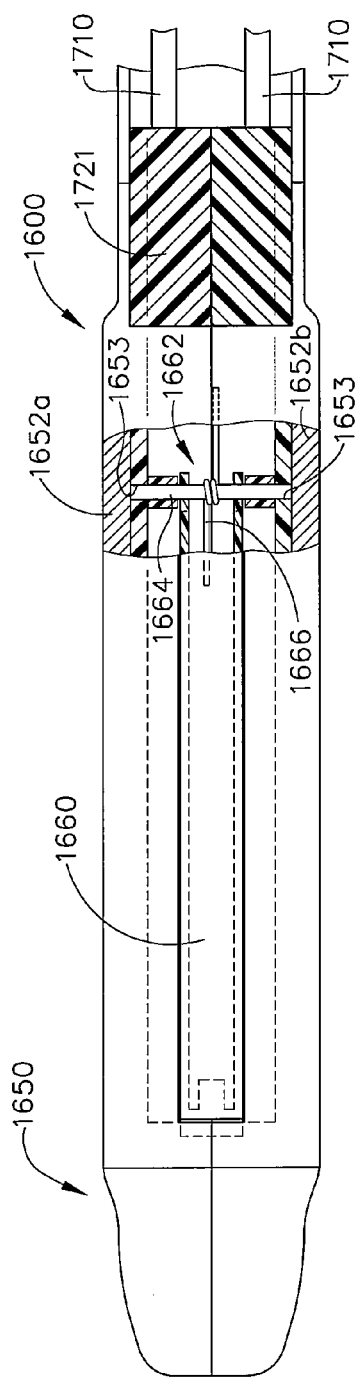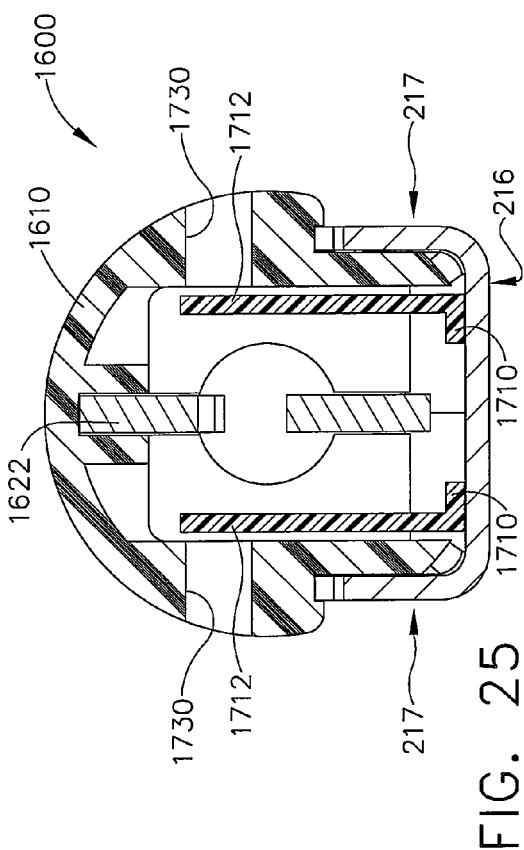
FIG. 24
FIG. 25

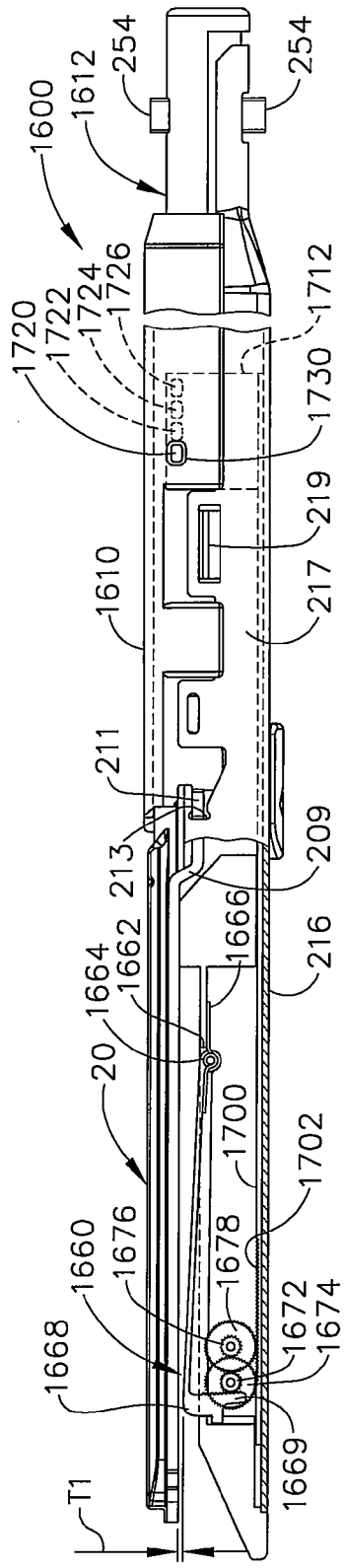
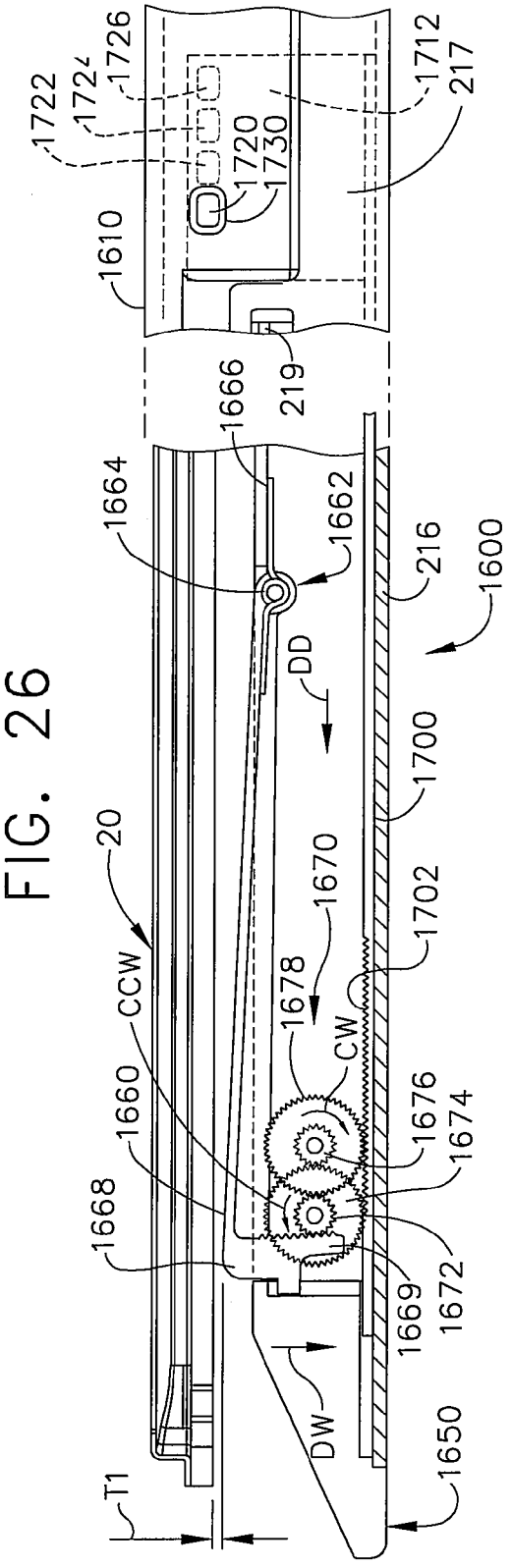
FIG. 26
FIG. 27

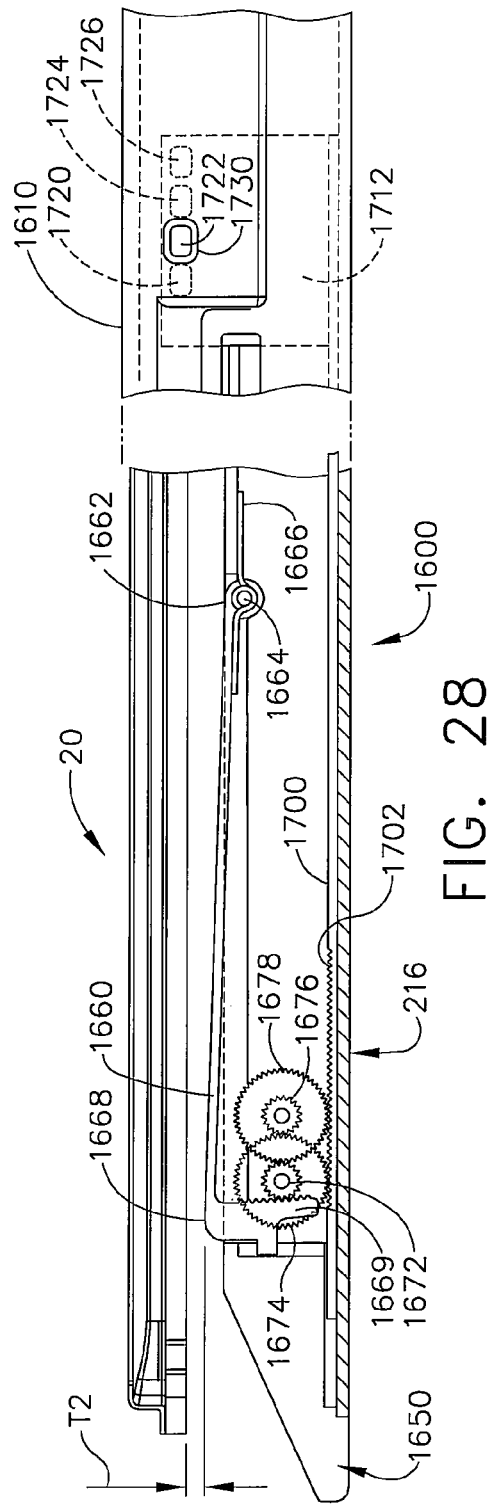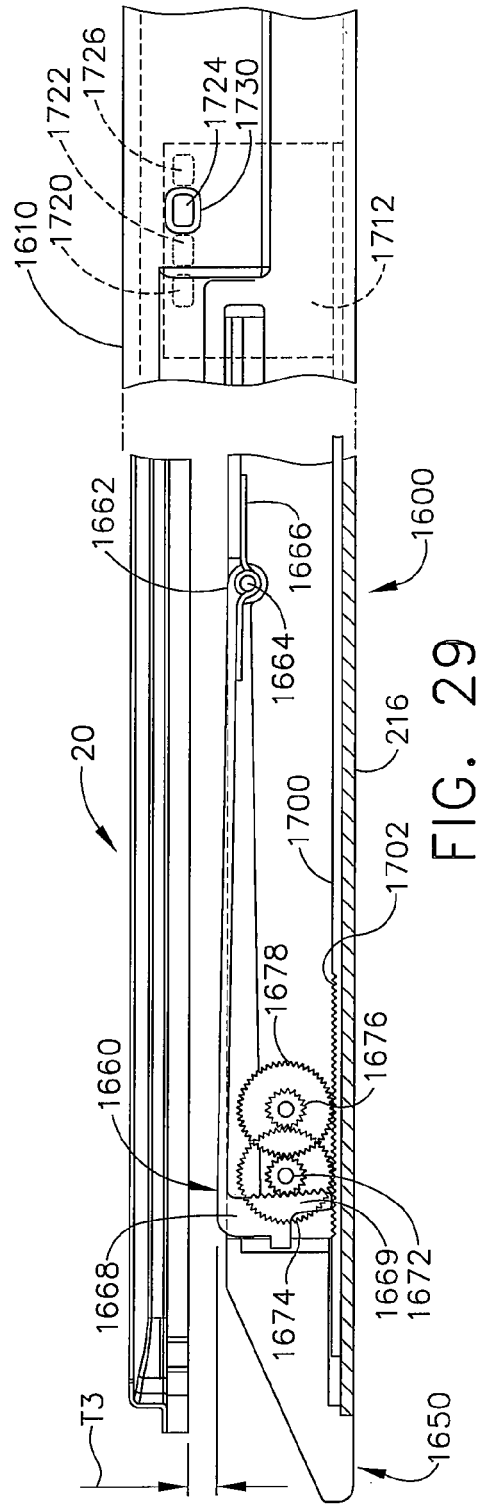

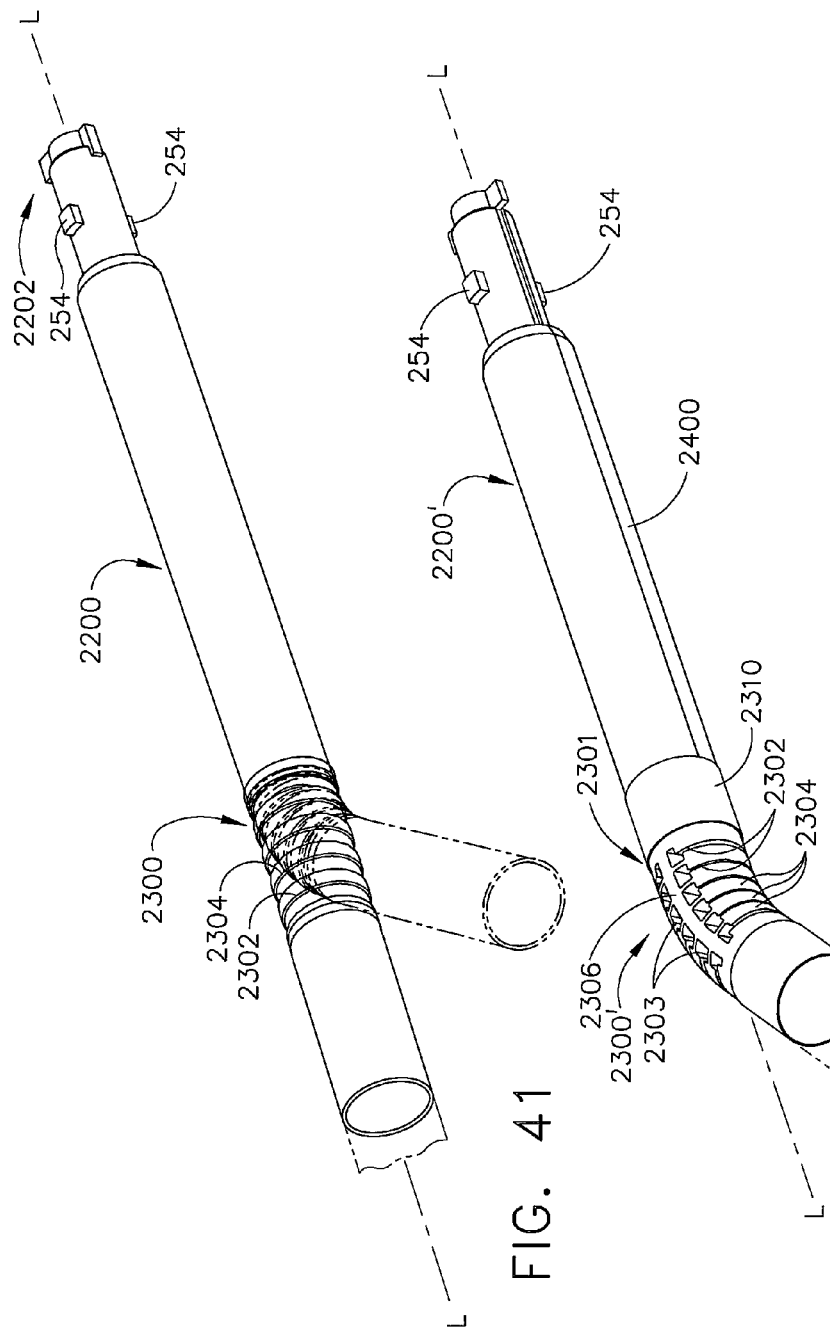

INTERCHANGEABLE TOOLS FOR SURGICAL INSTRUMENTS

FIELD OF THE INVENTION

The present invention relates in general to surgical instruments including, but not limited to, surgical instruments normally used with disposable cutting and stapling units that are capable of applying lines of staples to tissue while cutting the tissue between those staple lines and, more particularly, to a collection of interchangeable tools for use with such instruments.

COMMONLY OWNED PATENT APPLICATIONS

The Assignee of the subject application also co-owns the following U.S. Patent Applications which are herein incorporated by reference:

U.S. patent application Ser. No. 11/729,008, entitled Laparoscopic Tissue Thickness and Clamp Load Measuring Devices, filed Mar. 28, 2007, U.S. Patent Application Publication No. US 2009-0012556 A;

U.S. patent application Ser. No. 11/652,170, entitled Surgical Stapler With Tapered Distal End, filed Jan. 11, 2007, now abandoned;

U.S. patent application Ser. No. 12/031,628, entitled Disposable Motor Driven Loading Unit For Use With a Surgical Cutting and Stapling Apparatus to Kyle P. Moore et al., filed Feb. 14, 2008, now U.S. Pat. No. 7,793,812; and U.S. patent application Ser. No. 12/031,001, entitled Articulatable Loading Units For Surgical Stapling and Cutting Instruments to Jerome R. Morgan et al., filed Feb. 14, 2008 now abandoned.

BACKGROUND

Endoscopic surgeries are often preferred over traditional open surgical procedures because the smaller incision required by endoscopic surgical procedures tends to reduce the post-operative recovery time and complications. A variety of surgical procedures are currently performed by laparoscopic or other endoscopic techniques. Such procedures may include, for example, intestinal and stomach operations such as removal of colon cancer, hernia repairs, stomach stapling, removal of gall bladder, Ob/Gyn related surgeries as well as other procedures, such as those involving manipulations of a patient's spleen, liver, lung, heart, etc.

Consequently, significant development has gone into a range of endoscopic surgical instruments that are suitable for precise placement of a distal end effector at a desired surgical site through a cannula of a trocar that has been inserted into a patient. These distal end effectors engage or interact with the tissue in a number of ways to achieve a desired diagnostic or therapeutic effect. Such devices are often configured to perform a single type of surgical action (e.g., endocutter, grasper, cutter, staplers, clip applier, access device, drug/gene therapy delivery device, and energy device using ultrasound, RF, laser, etc.) which often requires the clinician to use several different instruments that are each only adapted to perform one action during a single operation. For example, U.S. Pat. No. 5,352,235; U.S. Pat. No. 5,383,895; and U.S. Pat. No. 5,728,121 each disclose dedicated grasping instruments that may be used for endoscopic and laparoscopic procedures. For those procedures requiring the removal of tissue or specimens from the body (e.g., removal of a diseased gall bladder, appendix, etc.), dedicated specimen retrieval instruments such as those disclosed in U.S. Pat. No. 6,406,440 have been developed. For procedures requiring the cutting and severing of tissue, dedicated scissor instruments such as those described in U.S. Pat. No. 6,168,605 have also been developed.

For those procedures involving the cutting and stapling of tissue, various surgical stapling devices have been designed. Such surgical stapling devices commonly include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One form of surgical cutting and stapling device is disclosed in U.S. Pat. No. 6,905,057. Such devices have a dedicated reusable drive and knife beam and are designed to be used with replaceable staple cartridges. Removable cartridges constructed to measure tissue thickness such as those disclosed in U.S. patent application Ser. No. 11/729,008, entitled Laparoscopic Tissue Thickness and Clamp Load Measuring Devices, have also been designed for use with such instruments. Alternative curved end effector arrangements such as those disclosed in U.S. patent application Ser. No. 11/729,008, entitled Surgical Stapler With Tapered Distal End, also have dedicated reusable knife and drive beam arrangements for use with removable/replaceable staple cartridges.

Other types of surgical stapling devices such as those disclosed in U.S. Pat. No. 5,865,361 are configured to operate with disposable loading units (DLU's) that are constructed to support a dedicated staple cartridge and knife assembly therein. Once the procedure is completed, the entire DLU is discarded. Such instruments that are designed to accommodate DLU's purport to offer the advantage of a "fresh" knife blade for each firing of the instrument. The reusable hand piece portion of such surgical stapling instruments was limited to use in connection with disposable loading units that were constructed to cut and staple tissue. Thus, for operations that involve various actions and procedures (e.g., grasping and manipulating tissue, cutting tissue, removal of tissue, applying clips and/or staples, cauterization of tissue, delivery of drugs and medicaments, etc.) a collection of different surgical instruments that are designed specifically to perform one of those actions in the past were required to be on hand.

Thus, there is a need for different types of interchangeable surgical tool attachments that may be used with a single surgical instrument hand piece.

SUMMARY

In one general aspect of various embodiments of the present invention, there is provided a surgical tool for use with a surgical instrument that has a handle assembly that operably supports a drive system therein for generating drive motions upon actuation of a movable handle portion thereof. The surgical instrument further has an elongated body that operably supports a control rod therein for transferring the drive motions. Various embodiments of the surgical tool comprise a housing that is removably couplable to the elongated body. A drive assembly may be operably supported in the housing and is removably couplable to the control rod. A pair of non-staple forming jaws are operably coupled to the drive assembly such that upon application of a drive motion to the drive assembly in a first direction the non-staple forming jaws each simultaneously move in a closing direction toward each other and upon application of another drive motion in a second direction, the non-staple forming jaws each simultaneously move in an opening direction away from each other.

In still another general aspect of various embodiments of the present invention, there is provided a surgical tool for use with a surgical instrument that has a handle assembly that operably supports a drive system therein for generating drive motions upon actuation of a movable handle portion thereof. The surgical instrument may further have an elongated body that operably supports a control rod therein for transferring the drive motions. Various embodiments of the surgical tool may comprise a carrier that has a housing coupled thereto. The housing may be movably couplable to the elongated body. A drive assembly may be operably supported in the housing and carrier and be removably couplable to the control rod. A non-staple forming anvil may be movably supported on the carrier and configured to operably interact with the drive assembly to selectively move the non-staple forming anvil toward and away from the carrier. A tissue thickness measuring cartridge may be supported in the carrier. The tissue thickness measuring cartridge may have an indicator member that interacts with the housing to provide an indication of a thickness range of tissue clamped between the non-staple forming anvil and the tissue thickness measuring cartridge.

In another general aspect of various embodiments of the present invention, there is provided a surgical tool for use with a surgical instrument that has a handle assembly that operably supports a drive system therein for generating drive motions upon actuation of a movable handle portion thereof. The surgical instrument may further have an elongated body that operably supports a control rod therein for transferring the drive motions. In various embodiments, the surgical tool comprises a housing that is directly couplable to the elongated body. A drive assembly may be operably supported in the housing and carrier. The drive assembly may be removably couplable to the control rod. A staple-forming anvil may be non-movably supported by the housing. A plurality of staples may be supported in a distal end of the housing and be oriented to be sequentially driven into the staple-forming anvil upon application of a drive motion to the drive assembly.

In another general aspect of various embodiments of the present invention, there is provided a surgical tool for use with a surgical instrument that has a handle assembly that operably supports a drive system therein for generating drive motions upon actuation of a movable handle portion thereof. The surgical instrument may further have an elongated body that operably supports a control rod therein for transferring the drive motions. In various embodiments, the surgical tool comprises a housing that is directly couplable to the elongated body. A pair of opposed, moveable jaws may be attached to and extend from the shaft. The jaws are configured to receive each of the surgical clips serially therein when the jaws are in an open position. The jaws may also form each of the surgical clips received serially therein when the jaws are moved to a closed position. A moveable forming mechanism may be removably couplable to the control rod when the housing is coupled to the elongated body. The forming mechanism may be configured to move the jaws from the open position to the closed position upon application of a first drive motion from the control rod so as to form each of the surgical clips received serially therein. The forming mechanism may be further configured to move from the closed position to the open position upon application of a second drive motion to the forming mechanism by the control rod. A feeding mechanism may operatively interact with the movable forming mechanism. The feeding mechanism may have a feed plate that is movable in response to movement of the forming mechanism and may be releasably coupled to a clip pusher of the feed mechanism. The clip pusher may be stationary and uncoupled from the feed plate upon application of the first drive motion to the forming mechanism. The clip pusher may be moveable and operatively coupled to the feed plate upon application of the second drive motion to the movable forming mechanism so as to move each of the surgical clips serially from the shaft into the jaws.

In connection with another general aspect of the present invention there is provided a surgical tool for use with a surgical instrument that has a handle assembly that operably supports a drive system therein for generating drive motions upon actuation of a movable handle portion thereof. The surgical instrument may further have an elongated body that operably supports a control rod therein for transferring the drive motions. Various embodiments of the surgical tool of the present invention may comprise a carrier that has a housing coupled thereto. The housing may be removably couplable to the elongated body. A drive assembly may be operably supported in the housing and carrier and also be removably couplable to the control rod. A staple forming anvil may be movably supported on the carrier and operably interact with the drive assembly to selectively move the staple forming anvil toward and away from the carrier. A staple-supporting cartridge that has a radius of curvature may be supported in the carrier. The staple-supporting cartridge may have a curved slot therethrough defining a curved passage for receiving a distal end of the drive assembly therethrough upon application of a drive motion thereto.

In accordance with another general aspect of the present invention there is provided a surgical tool for use with a surgical instrument that has a handle assembly that operably supports a drive system therein for generating drive motions upon actuation of a movable handle portion thereof. An elongated body may operably support a control rod therein for transferring the drive motions. Various embodiments of the surgical tools may comprise a housing that is removably couplable to the elongated body. A syringe body may be coupled to the housing. A hollow needle may protrude from the syringe body. A drive assembly may be operably supported in the housing and may be removably couplable to the control rod. A syringe plunger may be movably supported in the syringe body and may be coupled to the drive assembly for selective movement therewith.

In accordance with still another general aspect of the present invention there is provided a surgical tool for use with a surgical instrument that has a handle assembly that operably supports a drive system therein for generating drive motions upon actuation of a movable handle portion thereof. An elongated body may operably support a control rod therein for transferring the drive motions. Various embodiments of the surgical tool may comprise a housing that is removably couplable to the elongated body. A non-staple applying end effector may operably protrude from a distal end of the housing. The non-staple applying end effector may support at least one electrically powered member. A battery may be movably supported within the housing and be configured to electrically communicate with the at least one electrically powered member. The battery may be removably couplable to the control rod such that upon application of a first drive motion thereto, the battery applies power to the electrical powered member and, upon application of a second drive motion thereto, the battery discontinues the application of power to the electrically powered member.

In accordance with another general aspect of the present invention there is provided a surgical tool system that includes a surgical instrument that may comprise a handle assembly that has a drive system operably supported therein for generating drive motions upon actuation of a movable handle portion that is operably coupled to the handle assembly. An elongated body may protrude from the handle assembly and a control rod may be operably supported in the elongated body. The control rod may interface with the drive system for receiving the drive motions therefrom. The system may further include at least two surgical tools that are selected from the group of surgical tools consisting of: manipulators, nippers, scissors, endocutters, tissue thickness measurement devices, staple appliers, clip appliers, syringe glue/sealant/drug/medicament appliers and cauterization devices wherein each surgical tool within the group of surgical tools at least has a housing that is removably couplable to the elongated body and a drive assembly that is removably couplable to the control rod for receiving the drive motions therefrom.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of various embodiments of the invention given above, and the detailed description of the embodiments given below, serve to explain various principles of the present invention.

FIG. 8 is a perspective view of another surgical tool embodiment of the present invention.

FIG. 9 is a cross-sectional view of the surgical tool embodiment of FIG. 8.

FIG. 13 is a perspective view of another surgical tool embodiment of the present invention.

FIG. 14 is a cross-sectional view of the surgical tool embodiment of FIG. 13 with some components thereof shown in full view for clarity.

FIG. 18 is another side elevational view of the surgical tool embodiment of FIGS. 15 and 16 with a portion thereof shown in cross-section and with the anvil assembly shown in a first closed position with no tissue clamped therein.

FIG. 19 is an enlarged view of the distal end of the surgical tool embodiment depicted in FIG. 18.

FIG. 20 is a cross-sectional view of the surgical tool of FIG. 18 taken along line 20-20 in FIG. 18.

FIG. 21 is an enlarged view of the distal end portion of the surgical tool shown in FIG. 20.

FIG. 24 is a cross-sectional view of a portion of the surgical tool of FIG. 17 taken along line 24-24 in FIG. 17.

FIG. 25 is a cross-sectional view of a portion of the surgical tool of FIG. 17 taken along line 25-25 in FIG. 17.

FIG. 26 is a side elevational view of the surgical tool embodiment of FIGS. 15-25 with anvil assembly in a closed position for clamping tissue having a first thickness range therein.

FIG. 27 is an enlarged view of the distal end of the surgical tool embodiment depicted in FIG. 26.

FIG. 28 is a side elevational view of the surgical tool embodiment of FIGS. 15-27 with the anvil assembly in a closed position for clamping tissue having a second thickness range therein.

FIG. 29 is a side elevational view of the surgical tool embodiment of FIGS. 15-28 with the anvil assembly in a closed position for clamping tissue having a third thickness range therein.

FIG. 41 is a perspective view of an alternate housing embodiment of the present invention with a portion thereof shown in phantom lines to illustrate the ability to articulate about an articulation member formed therein.

FIG. 42 is a perspective view of another alternate housing embodiment of the present invention.

DETAILED DESCRIPTION

Figure 1:
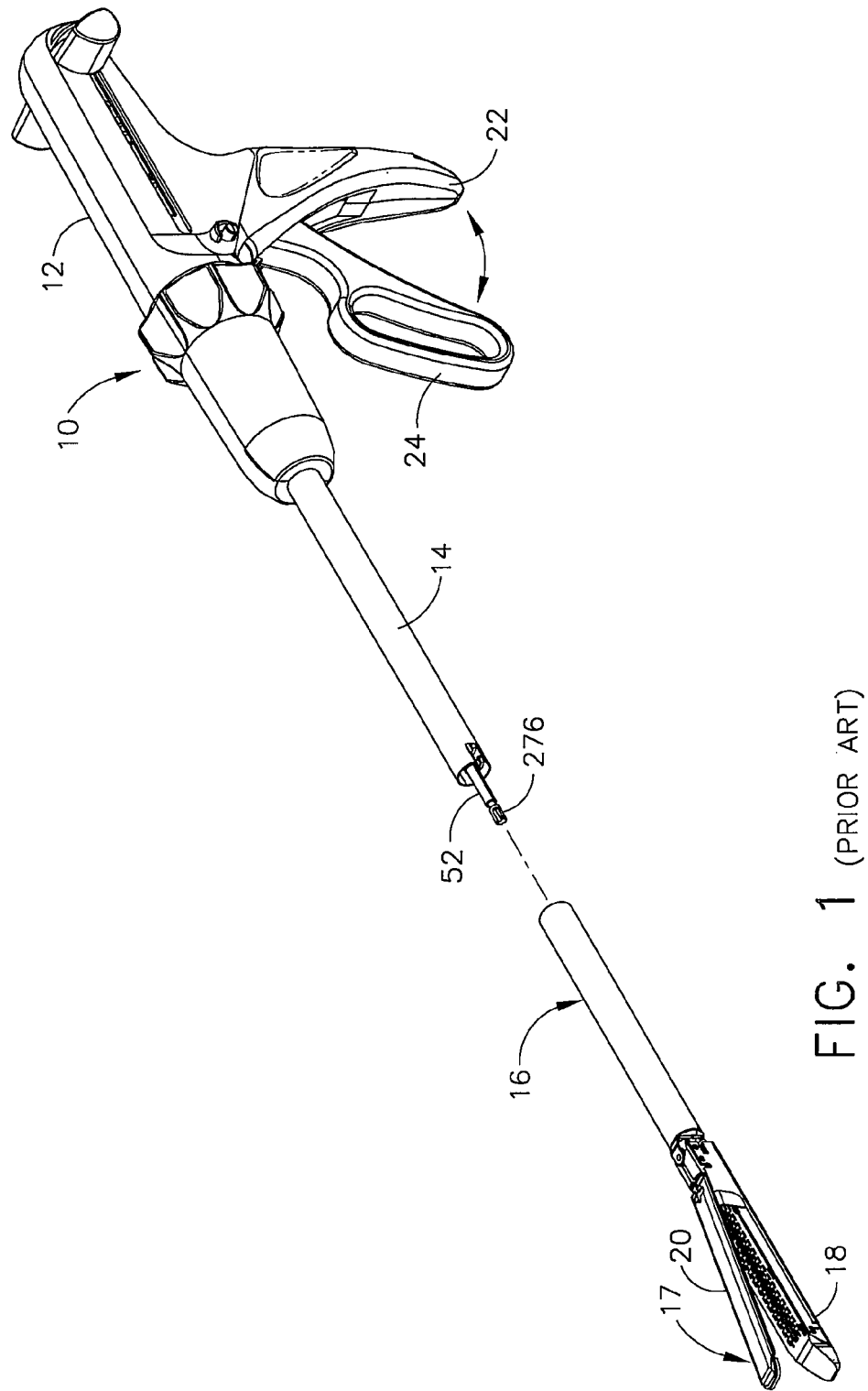
FIG. 1 is a perspective view of a prior surgical cutting and stapling apparatus.

Turning to the Drawings, wherein like numerals denote like components throughout the several views, FIG. 1 depicts a prior surgical instrument 10 that includes a housing assembly 12 and an elongated body 14 that protrudes therefrom. Also shown in FIG. 1 is a prior disposable loading unit 16 that comprises a single-use endocutter for cutting tissue and applying lines of staples on each side of the cut. The disposable loading unit 16 includes a tool assembly 17 having a cartridge assembly 18 housing a plurality of surgical staples and an anvil assembly 20 movably secured in relation to cartridge assembly 18. In various embodiments, the conventional surgical instrument 10 and the disposable loading unit 16 may comprise the surgical instrument and disposable loading units described in U.S. Pat. No. 5,865,361, the disclosure of which has been herein incorporated by reference. Thus, the present Detailed Description will not specifically discuss the various components of the surgical instrument 10 and the disposable loading unit 16 and their operation herein beyond what is necessary to describe the operation of the various surgical tool embodiments of the present invention which may be used with a surgical instrument 10.

As the present Detailed Description proceeds, it will be appreciated that the terms "proximal" and "distal" are used herein with reference to a clinician gripping a handle assembly 12 of the surgical instrument 10 to which a particular surgical tool is operably coupled. Thus, the surgical tool is "distal" with respect to the more proximal handle assembly 12. It will be further appreciated that, for convenience and clarity, spatial terms such as "vertical", "horizontal", "up", "down", "right", and "left" are used herein with respect to the drawings. However, surgical tools and instruments are used in many orientations and positions, and these terms are not intended to be limiting and absolute.

Figure 2:
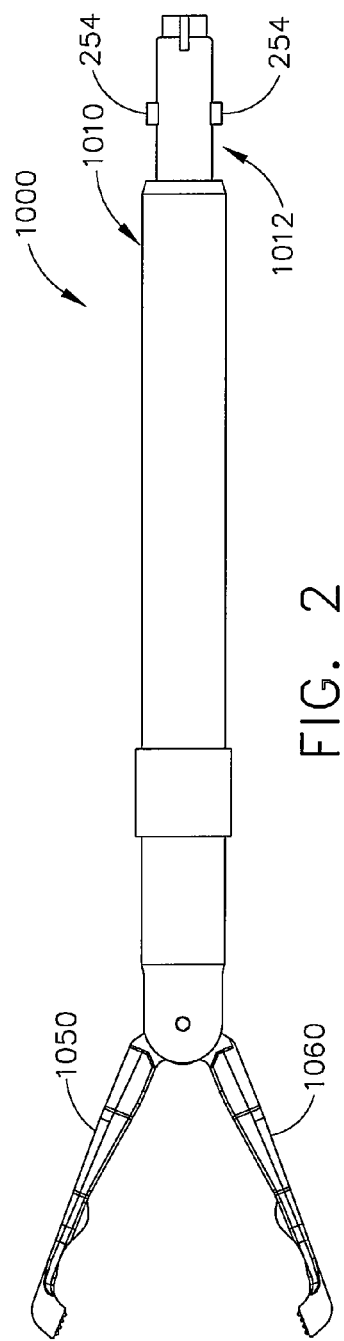
FIG. 2 is a side view of a surgical tool embodiment of the present invention.
Figure 3:
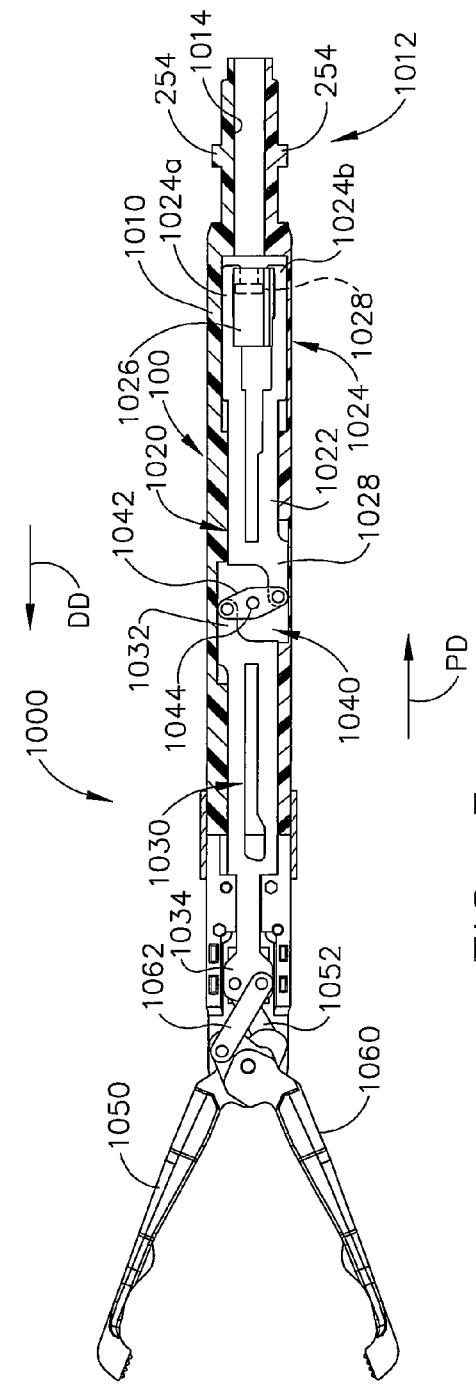
FIG. 3 is a cross-sectional view of the surgical tool embodiment of FIG. 2 with some components thereof shown in full view for clarity.
Figure 4:
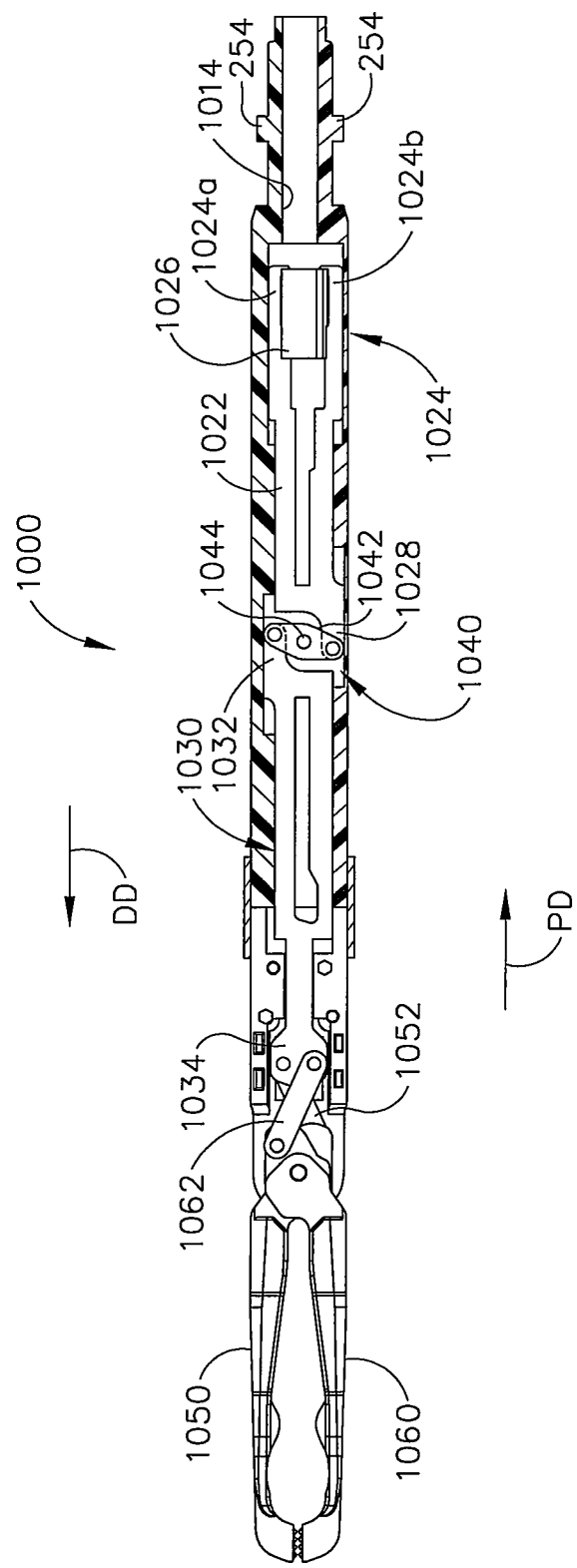
FIG. 4 is another cross-sectional view of the surgical tool embodiment of FIGS. 2 and 3 in a closed position.

FIGS. 2-4 depict a surgical tool 1000 of an embodiment of the present invention that may be operably coupled to the surgical instrument 10 and used to manipulate tissue, organs, etc. As can be seen in those Figures, the surgical tool 1000 may include a housing 1010 that has a proximal end 1012 that is configured for removable attachment to the elongated body 14 of the surgical instrument 10. In particular, the proximal end 1012 may have engagement nubs 254 formed thereon which serve to form a bayonet-type coupling with the distal end of the elongated body portion 14 of the surgical stapling apparatus as described in U.S. Pat. No. 5,865,361.

The surgical tool 1000 includes a drive assembly 1020 that may include a proximal drive beam segment 1022 that is coupled to a distal drive beam segment 1030 by a reversing linkage assembly 1040. The drive beam segments 1020, 1030 may each be constructed from a single sheet of material or, preferably, from multiple stacked sheets. However, drive beam segments 1020, 1030 may be fabricated from other suitable materials and arrangements. As can be seen in FIG. 3, the proximal drive beam segment 1022 has an engagement section 1024 formed thereon that may include a pair of engagement fingers 1024a and 1024b that are dimensioned and configured to mountingly engage a drive member 1026. Drive member 1026 includes a proximal porthole 1028 configured to receive the distal end 276 of control rod 52 (See FIG. 1) when the proximal end 1012 of tool attachment 100 is coupled to the elongated body 14 of surgical apparatus 10. As can be seen in FIG. 3, the proximal end 1012 has a hollow passage 1014 therein through which the distal end 276 of the control rod 52 may extend.

The distal end of the proximal beam segment 1022 has a distally protruding tab 1028 that is pinned to a link 1042 of the reversing linkage assembly 1040. The link 1042 is pivotally attached to the housing 1010 by pin 1044 and is also attached to a proximal tab portion 1032 of distal drive beam segment 1030. The distal end 1034 of the distal drive beam segment 1030 may be pivotally attached to an upper non-staple forming manipulation jaw 1050 by a first pivot link 1052 and also attached to a lower non-staple-forming manipulation jaw 1060 by a second pivot link 1062. As used herein, the term "non-staple forming" refers to jaws that are designed to grip or manipulate tissue, but are not designed to form, support or drive staples, such as, for example, anvils, staple cartridges or portions of units designed to support staple cartridges.

FIGS. 2 and 3 illustrate the upper and lower manipulation jaws 1050, 1060 in an open orientation and FIG. 4 illustrates the upper and lower manipulation jaws 1050, 1060 in a closed orientation. Once the surgical tool 1000 is coupled to the elongated body 14 of the surgical apparatus 10 (and the distal end 276 of the control rod 52 is coupled to the drive member 2026), the clinician may move the upper and lower manipulation jaws 1050, 1060 between the open and closed positions by manipulating the movable handle portion 24 of the surgical apparatus 10. For example, pivoting the movable handle portion 24 toward the stationary portion 22 of the handle assembly 12, causes the control rod 52 to move the proximal drive beam segment 1022 in a "first" distal direction "DD". As the proximal drive beam segment 1022 moves in the first distal direction "DD", the reversing linkage 1040 pulls the distal drive beam segment 1030 in a "second" proximal direction "PD" which causes the links 1052, 1062 to each simultaneously move the upper and lower non-staple forming manipulation jaws 1050, 1060 toward each other to a closed orientation. Moving the movable handle 24 away from the stationary handle portion 22 causes the non-staple forming upper and lower manipulation jaws 1050, 1060 to each simultaneously move away from each other to the open position.

Figure 5:
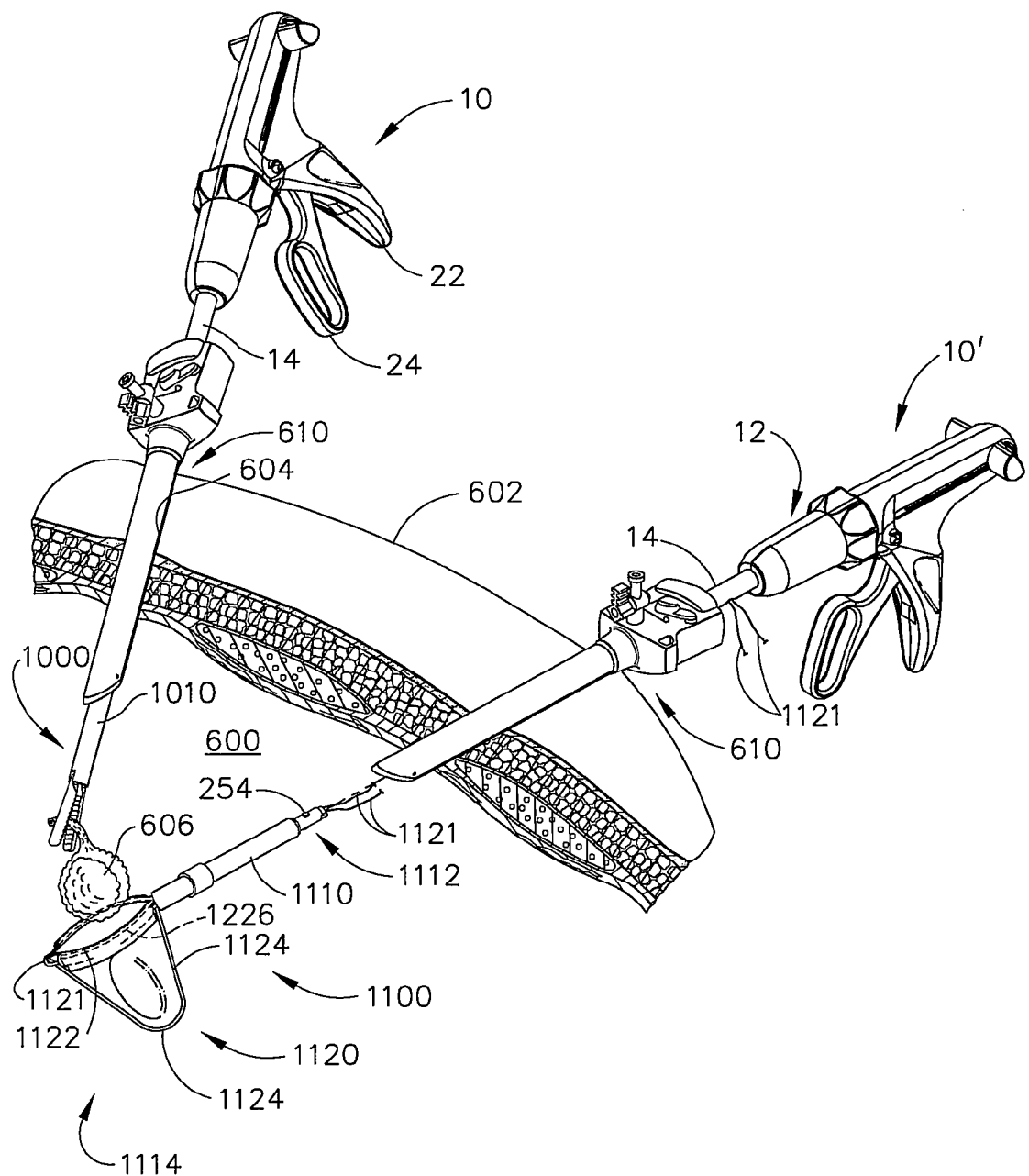
FIG. 5 is a perspective view showing one exemplary use of the surgical tool embodiment of FIGS. 2-4 in connection with another surgical tool embodiment of the present invention for removing tissue from a patient.

The person of ordinary skill in the art will understand that the non-staple forming upper and lower manipulation jaws 1050, 1060 may be provided in different shapes and sizes without departing from the spirit and scope of the present invention. For example, FIG. 5 illustrates one use of the surgical tool 1000 of the present invention in connection with the removal of tissue, etc. from a body cavity 600. More specifically, FIG. 5 illustrates use of a conventional first trocar 610 that is used to form a first passage 604 through a body wall 602 into the body cavity 600. A surgical tool 1000 of the present invention is attached to a first convention surgical apparatus 10. The surgical tool 1000 is then inserted through a cannula in the first trocar 610 and into the body cavity 600 to grasp and manipulate a portion of tissue 606.

Some medical procedures may require portions of diseased tissue or organs to be removed from the body cavity 600. To facilitate removal of small amounts of such tissue from the body cavity 600, another surgical tool 1100 of the present invention may be employed. As can be seen in FIG. 5, the surgical tool 1100 may include a housing portion 1110 that has a proximal end 1112 that has nubs 254 formed thereon to facilitate attachment to the elongated body portion 14 of a surgical apparatus 10' in the manner described above. Housing 1110 may have a hollow cavity therein, that would facilitate the movement of the control rod 52 therein. However, in various embodiments, the distal end 276 of the control rod is not directly coupled to any component within the housing.

Attached to the distal end 1114 of the housing 1110 is a specimen-retrieval pouch 1120 that may be formed from a collapsible pouch ring portion 1122 that has a flexible pouch member 1124 attached thereto. The collapsible pouch ring 1122 may be fabricated from spring arms 1226 or the like that would enable the pouch ring portion 1122 to collapse to enable the specimen retrieval pouch 1120 to be inserted into and retracted from a cannula of a conventional trocar 610 or the like.

Returning to FIG. 5, there is also illustrated a surgical tool 1100 of the present invention that has been attached to another conventional surgical instrument 10' that has been inserted through another conventional trocar 610. After the pouch assembly 1120 has been passed through the trocar cannula into the body cavity 600, the collapsible pouch ring 1122 springs open. The surgical tool 1000 may be employed to grasp diseased tissue 606 (e.g., gall stones, etc.) and place the diseased tissue 606 into the pouch assembly 1120 which may then be retracted out through the cannula of the second conventional trocar 610. A draw string 1121 extends around the pouch ring 1112 and through the housing 1110 to be threaded through a portion of the elongated body 14 and may exit through a hole therein adjacent the handle assembly 12. The draw string 1121 may be used to close the specimen retrieval pouch 1120 when removing the filled pouch 1120 from the body cavity.

Figure 6:
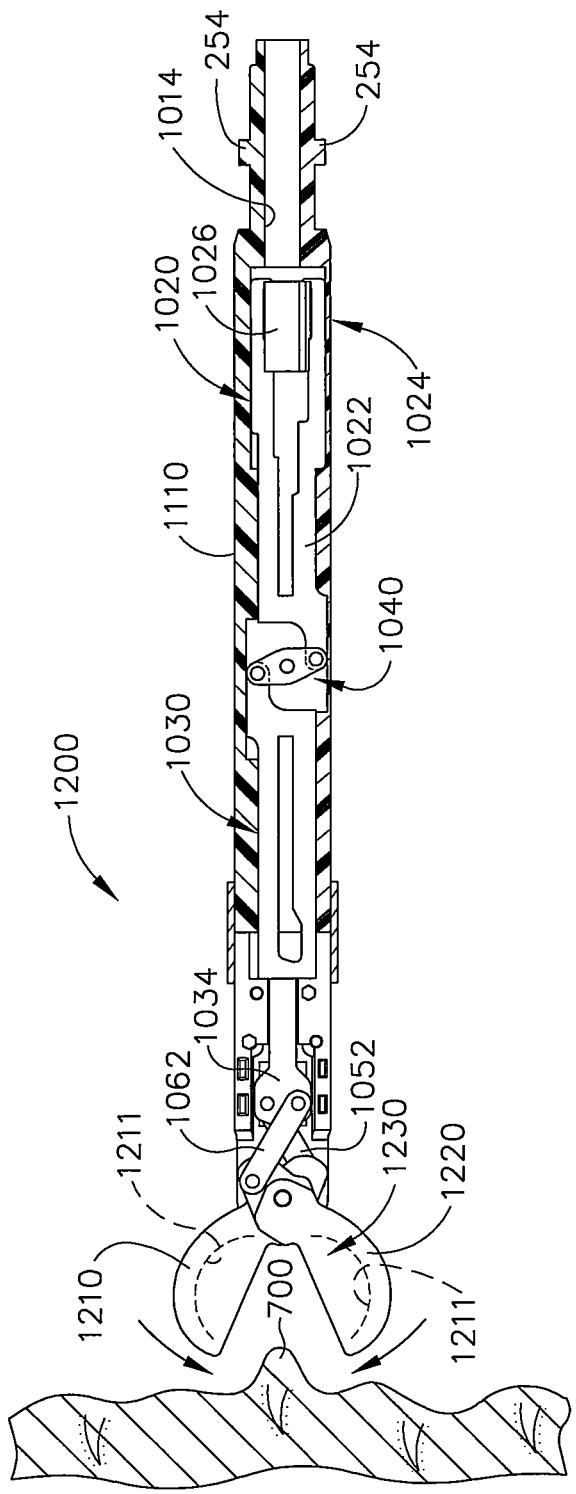
FIG. 6 is a cross-sectional view of another surgical tool embodiment of the present invention with some components thereof shown in full view for clarity.

Certain other medical procedures involve the cutting and removal of small portions of tissue such as the removal of a polyp 700 or the extraction of a small portion of tissue for testing. A surgical tool embodiment 1200 of the present invention may be used to perform such activities. More specifically and with reference to FIG. 6, a surgical tool 1200 may include the housing portion 1110 and drive beam segments 1022, 1030 as was described above. The surgical tool 1200 is coupled to the elongated body portion 14 and the control rod 52 in the manner described above and is operated by moving the movable handle portion 24 toward and away from the stationary handle portion 22 as was also described above. However, in various embodiments, instead of having upper and lower manipulation jaws coupled thereto, an upper tissue nipping jaw 1210 and a lower tissue nipping jaw 1220 are attached to links 1052 and 1062, respectively. As can be seen in FIG. 6, the upper and lower tissue nipping jaws 1210 and 1220 are designed to nip tissue grasped therebetween. At least one of the jaws 1210, 1220 have a cavity portion 1211 therein for retrieving the nipped tissue. In the embodiment depicted in FIG. 6, each tissue nipping jaw 1210, 1220 have a cavity portion 1211 formed therein that cooperate to form a hollow receptacle area generally designated as 1230 when the jaws 1210, 1220 are substantially closed. Thus, after the tissue 700 has been nipped by closing the jaws 1210, 1220, the tissue 700 is then received in the hollow receptacle area 1230 for removal from the body.

Figure 7:
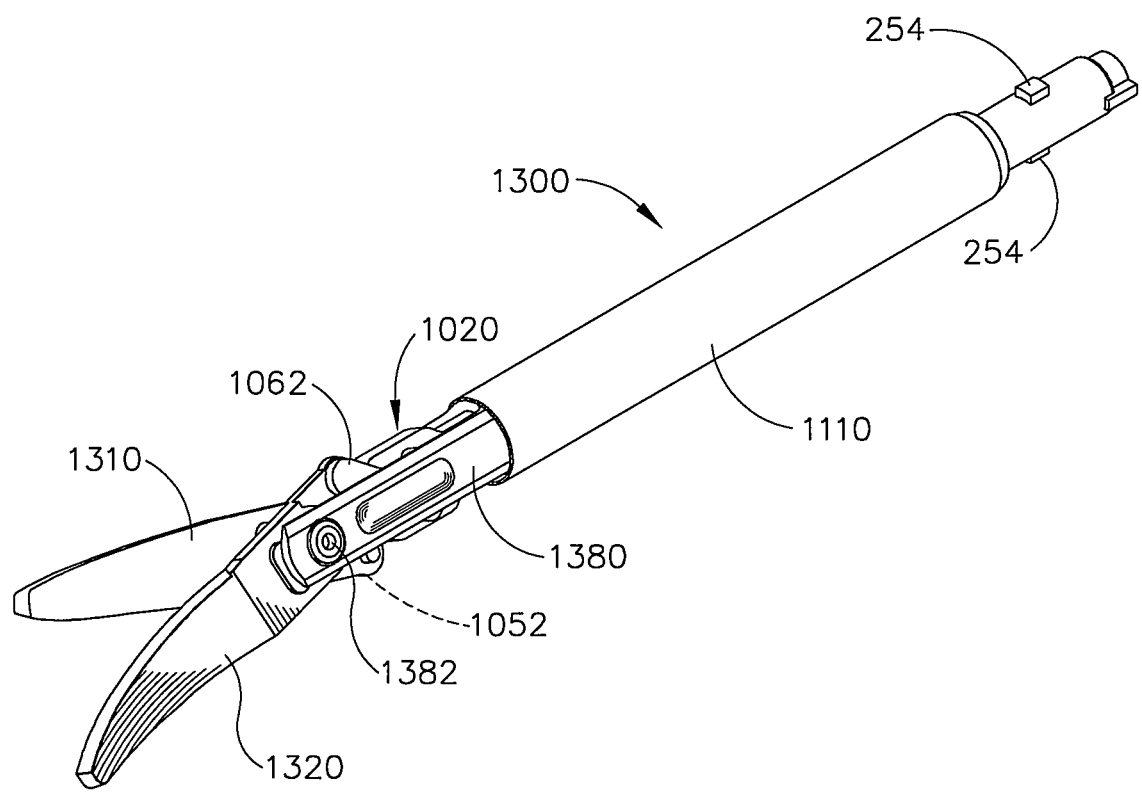
FIG. 7 is a perspective view of another surgical tool embodiment of the present invention.

FIG. 7 illustrates another surgical tool 1300 of the present invention that includes the housing portion 1110 and drive assembly 1020 as described above. As can be seen in FIG. 7, however, the surgical tool 1300 employs scissor jaws 1310 and 1320. In particular, the upper scissor jaw 1310 is attached to link 1052 and the lower scissor jaw is attached to link 1062. A support member 1380 protrudes out of the distal end of the housing portion 1110 and pivotally supports the scissor jaws 1310, 1320 about a pivot pin 1382 as shown. The surgical tool 1300 is coupled to the elongated body portion 14 and the control rod 52 of the surgical instrument 10 in the manner described above and is operated by moving the movable handle portion 24 toward and away from the stationary handle portion 22 as was also described above. Thus, the scissor jaws 1310, 1320 may be aligned with each other to enable the surgical tool 1300 to be inserted through a cannula (trocar) into the body cavity and then activated to cut tissue by moving the movable handle portion 24 of the surgical instrument 10.

FIGS. 8-12 illustrate another surgical tool 1400 that may be used with the conventional surgical instrument 10. As can be seen in those Figures, the surgical tool 1400 comprises a stapler for stapling tissue. More particularly and with reference to FIG. 8, the surgical tool 1400 may include a housing portion 1410 that has a proximal end portion 1412 that is configured for removable attachment to the elongated body 14 of the surgical instrument 10. In particular, the proximal end portion 1412 may have engagement nubs 254 formed thereon which serve to form a bayonet-type coupling with the distal end of the elongated body portion 14 of the surgical instrument 10 as described above. The surgical tool 1400 may include a drive assembly 1420 that includes an elongated drive beam 1422 that may be constructed from a single sheet of material or, preferably, from multiple stacked sheets. However, drive beam 1422 may be fabricated from other suitable materials and arrangements. As can be seen in FIG. 9, the drive beam 1422 has an engagement section 1424 formed thereon that may include a pair of engagement fingers 1424a and 1424b that are dimensioned and configured to mountingly engage a drive member 1426. Drive member 1426 includes a proximal porthole 1428 configured to receive the distal end 276 of control rod 52 (See FIG. 1) when the proximal end 1412 of the surgical tool 1400 is coupled to the elongated body 14 of a surgical instrument 10. As can be seen in FIG. 9, the proximal end 1412 has a hollow passage 1414 therein through which the distal end 276 of the control rod 52 may extend.

Figure 10:
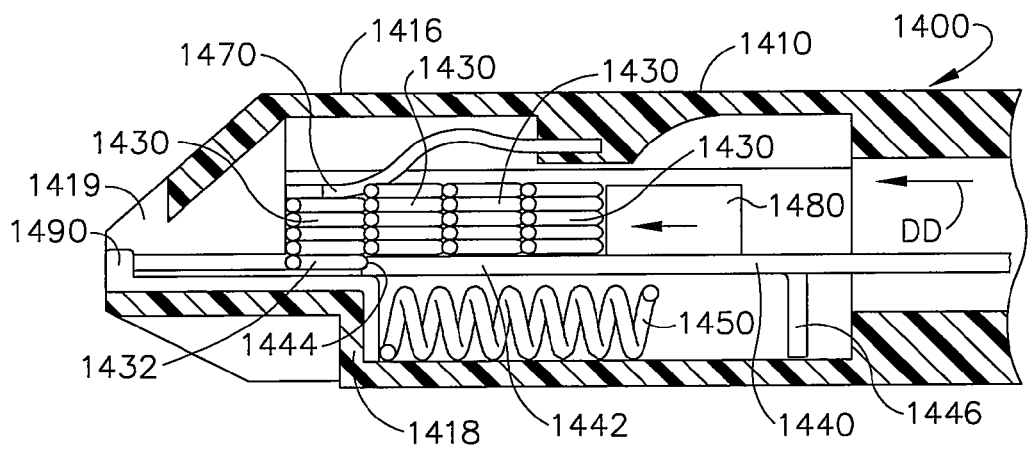
FIG. 10 is an enlarged cross-sectional view of the distal end of the surgical tool of FIGS. 8 and 9 in a pre-fired position.
Figure 11:
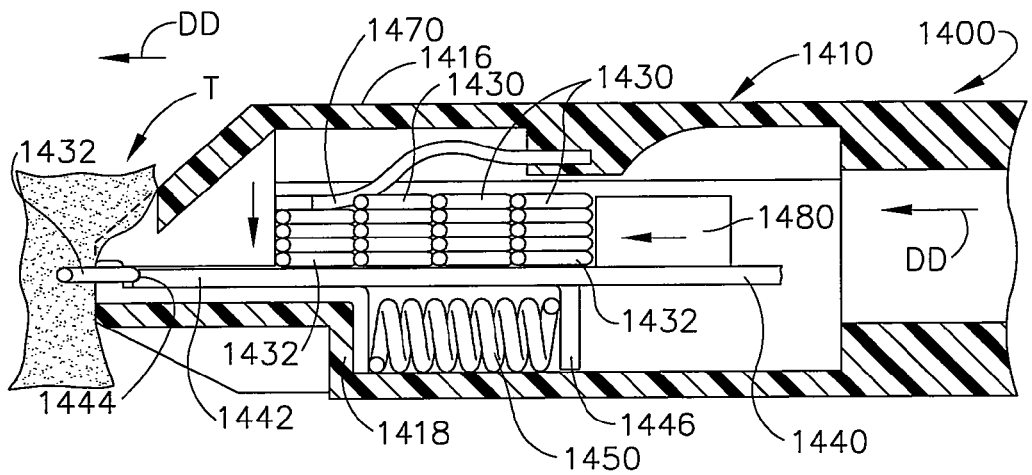
FIG. 11 is another enlarged cross-sectional view of the distal end of the surgical tool of FIGS. 8-10 wherein a staple is being fired into tissue.
Figure 12:
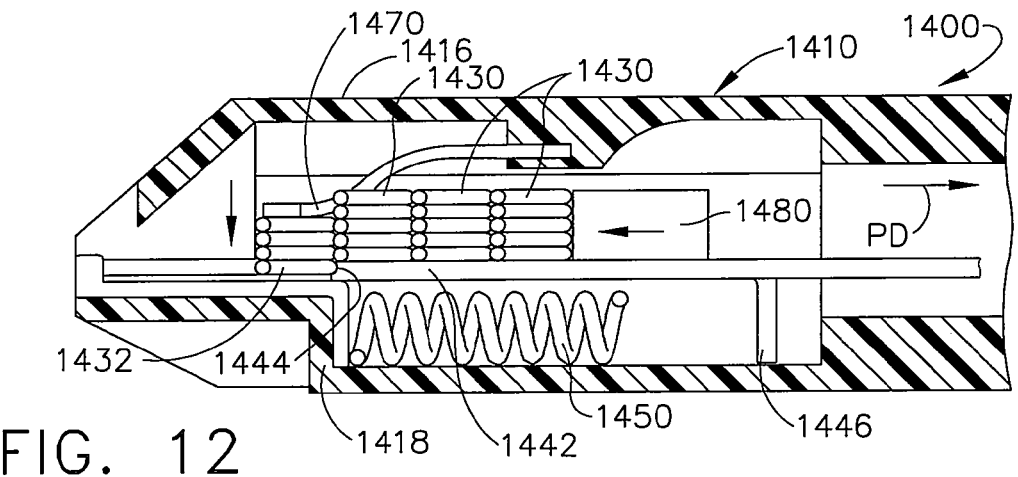
FIG. 12 is another enlarged cross-sectional view of the distal end of the surgical tool of FIGS. 8-11 after a first staple has been fired.
Figure 15:
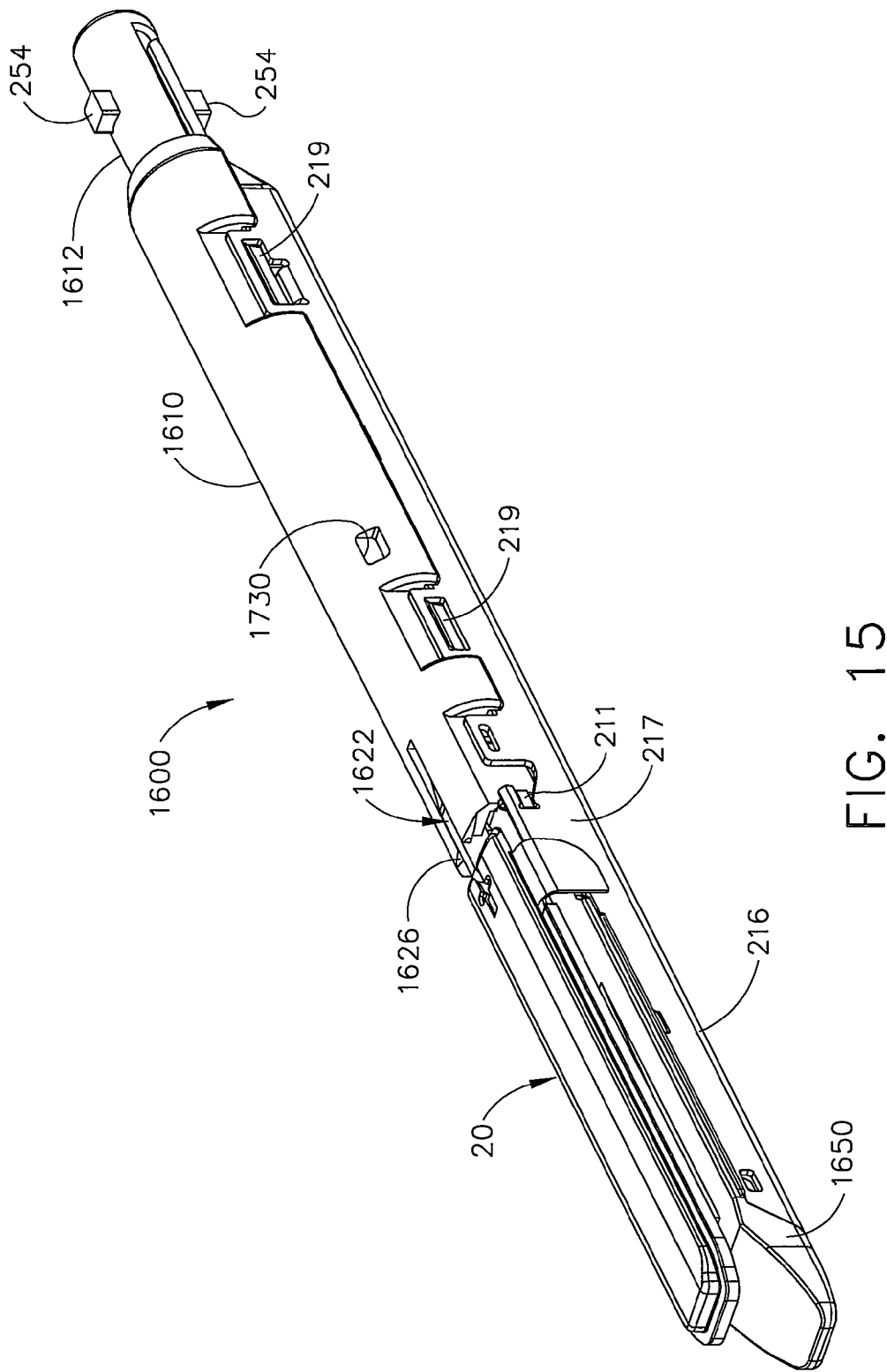
FIG. 15 is a perspective view of another surgical tool embodiment of the present invention.

As can also be seen in FIGS. 9-12, the housing 1410 has a distal end portion 1416 that operably houses columns 1430 of surgical staples 1432 therein. In various embodiments, the housing 1410 may be fabricated in multiple segments to permit installation of the staples 1432 therein. For single use embodiments, the staples 1432 may be installed at the factory and the housing portions permanently assembled together by adhesive, snaps, etc. In other embodiments, the housing portions may be removably coupled together to permit installation of additional staples 1432. As can also been in FIGS. 9-12, a staple driver 1440 is affixed to the distal end of the drive beam 1422. The distal end 1442 of the staple driver 1440 may have a staple-receiving notch 1444 formed therein as can be seen in FIGS. 10-12.

The surgical tool 1400 is coupled to the elongated body portion 14 and the control rod 52 of the surgical instrument 10 in the manner described above and is operated by moving the movable handle portion 24 toward and away from the stationary handle portion 22 as was also described above. A return spring 1450 is supported between a wall portion 1418 of the housing 1410 and a return tab portion 1446 on the staple driver 1440 to assist with returning the staple driver 1440 to the return position wherein another staple 1432 may drop into a firing position as shown in FIG. 10. As can be seen in FIG. 10, when in a firing position, the bottom staple 1432 in the distal-most column 1430 of staples 1432 has dropped into engagement with the staple-receiving notch 1444 in the staple driver 1440. A leaf-type feed spring 1470 may be provided to bias each succeeding staple 1432 in the distal-most column 1430 of staples downward toward the staple driver 1440. In addition, a spring assembly 1480 (illustrated in box-form in FIGS. 10-12) is mounted in the distal end portion 1416 of the housing 1410 to bias the columns 1430 of staples 1432 in the distal direction "DD" on the staple driver 1440 so that as one column of staples 1432 is depleted, the next adjacent column of staples 1432 is biased into the firing position shown in FIG. 10.

Thus, to use the surgical tool 1400, the distal end 1416 of the housing portion 1410 is brought into engagement with the tissue "T" to be stapled. See FIG. 11. As can be seen in FIGS. 10-12, the distal end portion 1416 has an angled end 1417 that has an opening 1419 therein to expose the staple 1432 being fired. As the staple 1432 is fired (i.e., driven in the distal direction "DD" by the staple driver 1440) through movement of the movable handle portion 24 of the surgical instrument 10, it is formed as it contacts a staple-forming anvil 1490 non-movably mounted within the housing 1410. FIG. 10 illustrates the surgical tool 1400 prior to firing. FIG. 11 illustrates firing a staple 1432 into the tissue "T". FIG. 12 illustrates the staple driver 11440 after is has been retracted to permit another staple 1432 to drop into a ready position. While the surgical tool 1400 is particularly well-suited for endoscopic procedures, those of ordinary skill in the art will also appreciate that the surgical tool 1400 may also be used to staple open incisions that do not require the surgical tool 1400 to be inserted through a cannula into a body cavity.

FIGS. 13 and 14 illustrate another surgical tool 1500 that may be used with the conventional surgical instrument 10. As can be seen in those Figures, the surgical tool 1500 comprises a syringe for deploying, for example, glue, sealant, a drug or other medicament. More particularly and with reference to FIG. 14, the surgical tool 1500 may include a housing portion 1500 that has a proximal end portion 1512 that is configured for removable attachment to the elongated body 14 of the surgical instrument 10. In particular, the proximal end portion 1512 may have engagement nubs 254 formed thereon which serve to form a bayonet-type coupling with the distal end of the elongated body portion 14 of the surgical stapling instrument 10 as described above. The surgical tool 1500 may include a drive assembly 1520 that comprises an elongated drive beam 1522 that may be constructed from a single sheet of material or, preferably, from multiple stacked sheets. However, drive beam 1522 may be fabricated from other suitable materials and arrangements. As can be seen in FIG. 14, the drive beam 1522 has an engagement section 1524 formed thereon that may include a pair of engagement fingers 1524a and 1524b that are dimensioned and configured to mountingly engage a drive member 1526. Drive member 1526 includes a proximal porthole 1528 configured to receive the distal end 276 of control rod 52 (See FIG. 1) when the proximal end 1512 of the surgical tool 1500 is coupled to the elongated body 14 of surgical instrument 10. As can be seen in FIG. 14, the proximal end 1512 has a hollow passage 1514 therein through which the distal end 276 of the control rod 52 may extend.

As can also be seen in FIGS. 13 and 14, a syringe body 1570 is attached to a distal end 1516 by a collar 1572 or other fastener arrangement. The collar 1572 may be affixed to the housing 1510 and syringe body 1570, by adhesive or other suitable arrangements. As can be seen in FIG. 14, a distal end 1523 of the drive beam 1522 is attached to a syringe plunger 1574 that is movably supported within the syringe body 1570. A hollow needle or cannula 1580 may be attached to the distal end of the syringe body 1570 as shown. The syringe body 1570 may be filled with a drug or medicament by first advancing the syringe plunger 1574 to the distal end of the syringe body 1570 by moving the movable handle 24 of the surgical instrument 10 (FIG. 1) toward the stationary handle portion 22 of the handle assembly 12. Thereafter, the pointed end 1582 of the needle 1580 may be inserted into a vial or reservoir of glue, sealant, drug or medicament (not shown). The clinician may then draw the material from the reservoir into the syringe body 1570 through the needle 1580 by moving the movable handle 24 away from the stationary portion 22 of the handle assembly 12 which serves to move the drive beam 1522 and the syringe plunger 1574 in the proximal direction "PD". Once the desired amount of drug or medicament has been drawn into the syringe body 1574, the clinician may then insert the surgical tool 1500 into the body cavity through a cannula or other opening and then expel the drug or medicament from the syringe body 1570 by again moving the movable handle 24 toward the stationary handle portion 22 of the handle assembly 12. A scale or other form of measuring indicia 1590 may be provided on the syringe body 1570 to enable the clinician to monitor the amount of glue, sealant, drug or medicament that has been discharged from the syringe body 1574.

When a surgical procedure involves stapling of tissue, the clinician must select the proper size of staple to use based upon the thickness of the tissue to be stapled. For example, staples that are commonly used for endoscopic procedures are generally manufactured in various sizes to provide various formed heights such as 0.75 mm, 1.0 mm, 1.5 mm, 2.0 mm, etc. The clinician must carefully match the size of the staple to the thickness of the tissue. If the staple is too large, the tissue may not be held together properly or if the staple is too small, it may tear through the tissue. In the past, however, the clinician often would have to estimate the tissue thickness and then hope that the estimate was sufficiently accurate. Thus, there is a need for a surgical tool that could be used in connection with a surgical instrument 10 that can accurately measure tissue thickness so that the appropriate size of staples may be used.

FIGS. 15-30 depict a surgical tool embodiment 1600 of the present invention that may be operably coupled to the surgical instrument 10 and used to measure the thickness of tissue "T" that may need to be cut and stapled. As can be seen in those Figures, the surgical tool 1600 may include a carrier 216 that has a housing 1610 attached thereto. The housing 1610 may be attached to the upstanding walls 217 of the carrier 216 by snap features 219 or other suitable means. The housing 1610 has a proximal end 1612 that is configured for removable attachment to the elongated body 14 of the surgical instrument 10. In particular, the proximal end 1612 may have engagement nubs 254 formed thereon which serve to form a bayonet-type coupling with the distal end of the elongated body portion 14 of the surgical instrument 10 as was described above.

Figure 16:
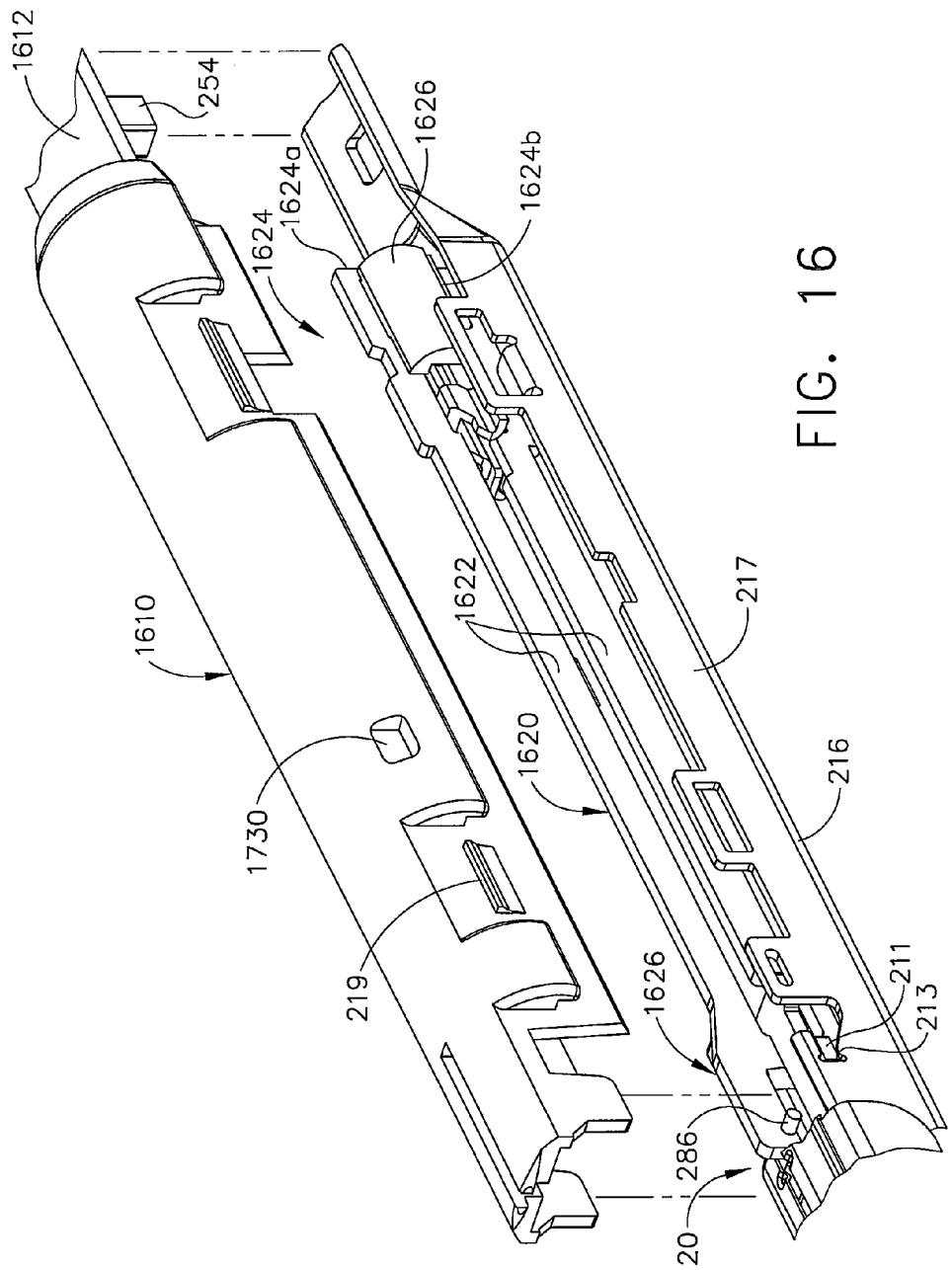
FIG. 16 is an exploded assembly view of a portion of the surgical tool embodiment of FIG. 15.
Figure 17:
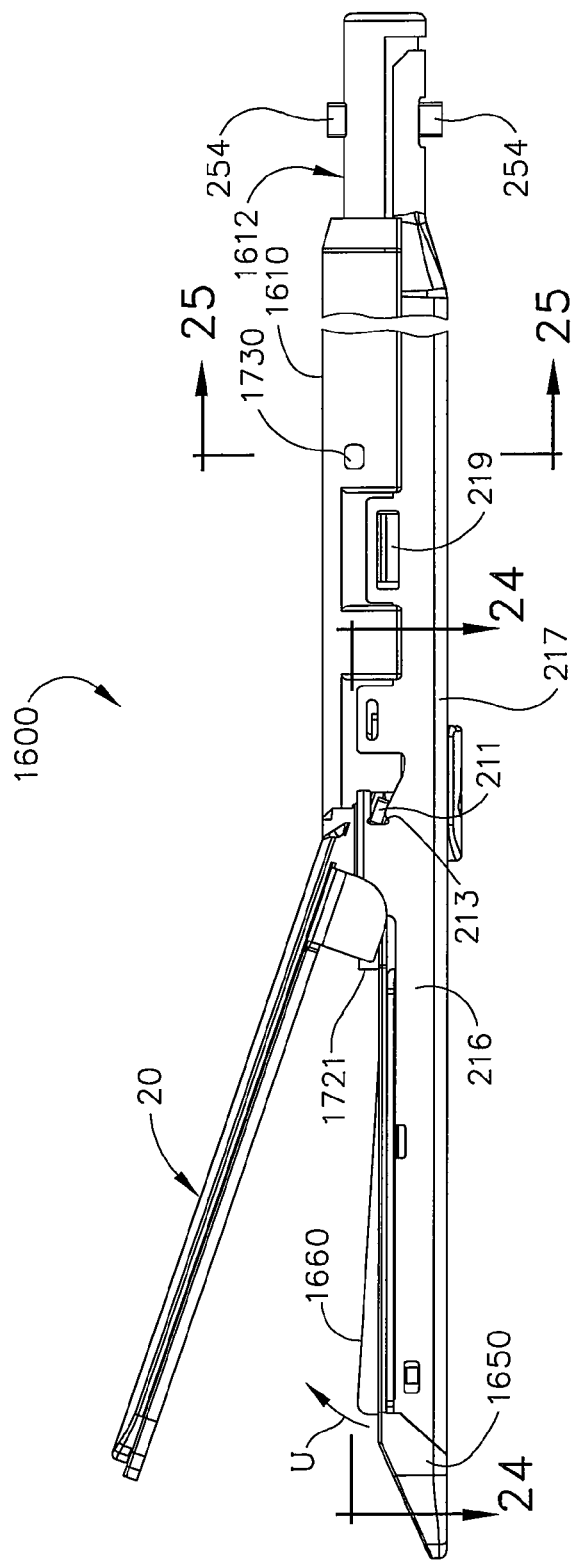
FIG. 17 is a side elevational view of the surgical tool embodiment of FIGS. 15 and 16 with the anvil assembly in an open position.

The surgical tool 1600 further includes a drive assembly 1620 that includes a drive beam 1622 that may be constructed from a single sheet of material or, preferably, from multiple stacked sheets. However, drive beam 1622 may be fabricated from other suitable materials and arrangements. As can be seen in FIG. 16, the drive beam segment 1622 has an engagement section 1624 formed thereon that may include a pair of engagement fingers 1624a and 1624b that are dimensioned and configured to mountingly engage a drive member 1626. Drive member 1626 includes a proximal porthole (not shown) to receive the distal end 276 of control rod 52 (See FIG. 1) when the proximal end 1612 of surgical tool 1600 is coupled to the elongated body 14 of the surgical instrument 10.

The distal end 1626 of the drive beam 1622 may have a camming pin or roller 286 (FIG. 16) arranged to engage a camming portion 209 (FIG. 18) of a non-staple forming anvil assembly 20 that is pivotally coupled to the carrier 216. A pair of pivot members 211 are formed on the anvil assembly 20 and are positioned within slots 213 formed in carrier 216 to guide the anvil portion between the open and clamped positions. As the drive beam 1622 is driven in the distal direction "DD" by moving the movable handle 24 toward the stationary handle portion 22 of the handle assembly 12 of the surgical instrument 10, the camming roller on the distal end of the drive beam 1622 engages the camming portion 209 of the anvil assembly 20 and causes the anvil assembly 20 to pivot to a given and repeatable closed position which forms a reference surface for establishing a thickness measurement.

Figure 22:
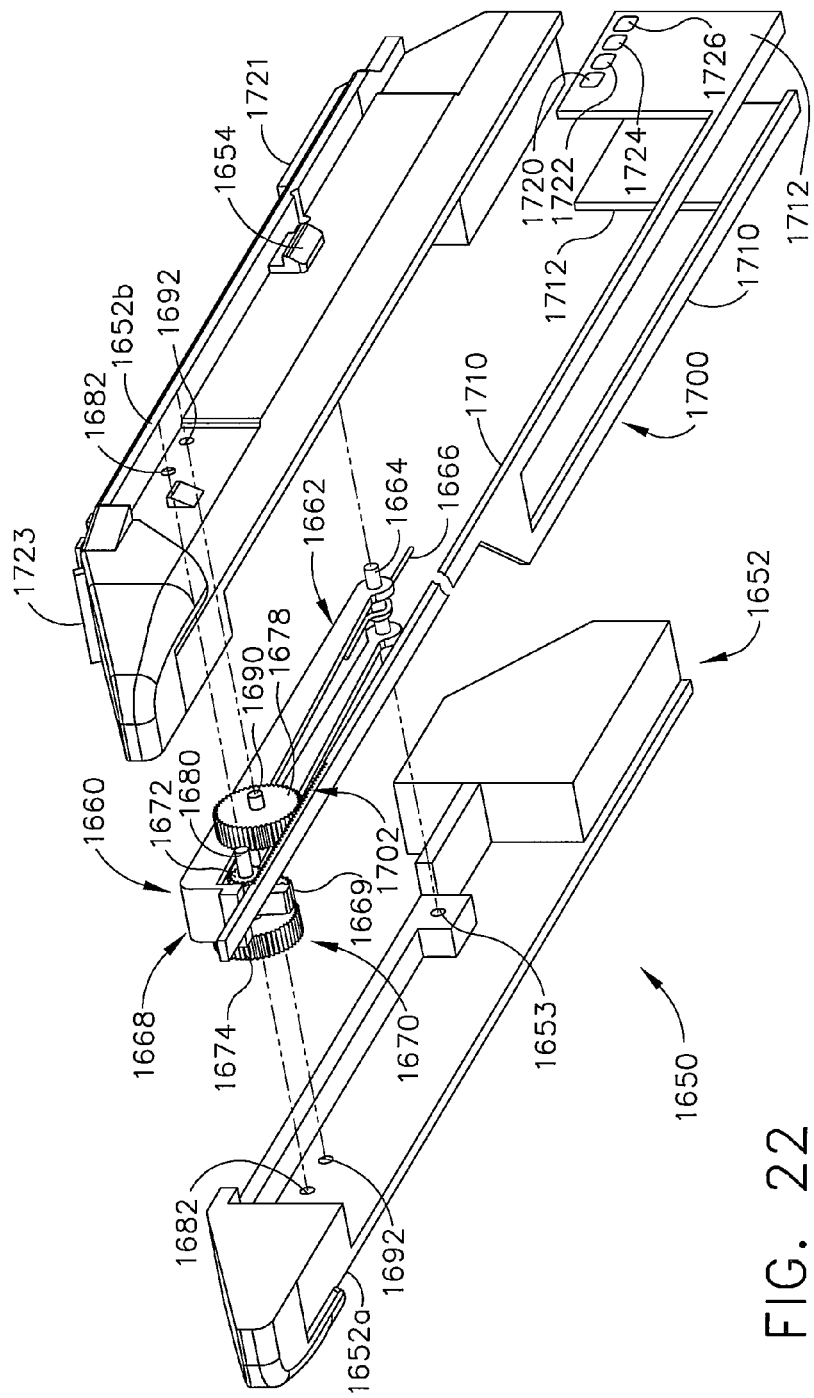
FIG. 22 is an exploded assembly view of a thickness measurement cartridge portion of the surgical tool of FIGS. 15-21.
Figure 23:
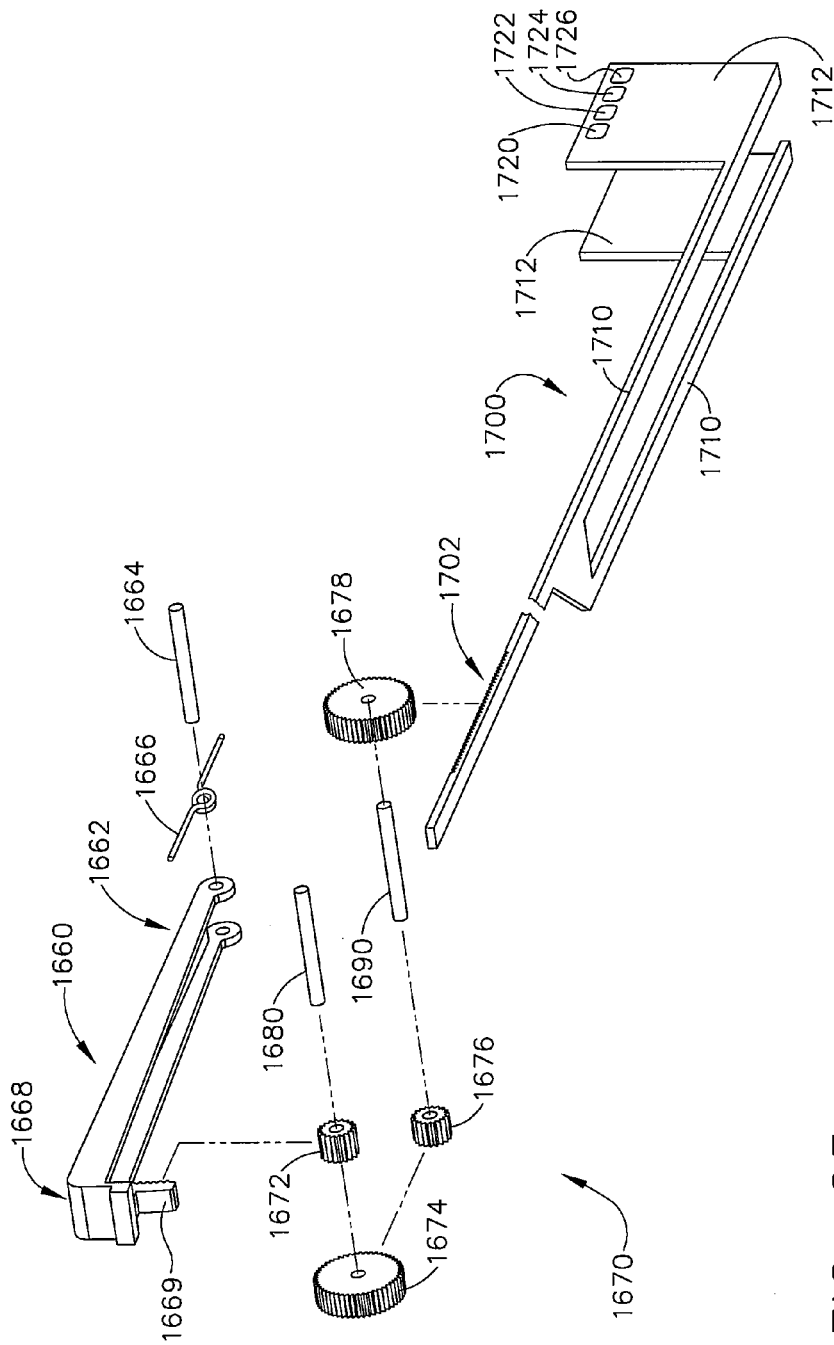
FIG. 23 is another exploded assembly view of portions of the thickness measurement cartridge of FIG. 21.

The surgical tool 1600 may further include a tissue thickness measuring cartridge 1650 that is supported within the carrier 216. As can be seen in FIGS. 18-22, the thickness measuring cartridge 1650 includes a body portion 1652 that is mounted within the carrier 216 and retained therein by snap features 1654 (FIG. 22) or other appropriate fastener arrangements. As can be seen in FIG. 22, for example, the cartridge body 1652 may be fabricated from two body segments 1652a, 1652b that may be fastened together by adhesive or other appropriate fasteners. As can be further seen in FIG. 22, the cartridge body 1652 operably supports a movable tissue measuring platform 1660. Tissue platform 1660 may be configured as shown in FIGS. 22 and 23 and have a proximal end portion 1662 that is coupled to the cartridge body portion 1652 by a hinge pin 1664. A platform spring 1666 may be journaled on the hinge pin 1664 to bias the tissue platform 1660 in a direction toward the anvil assembly 20 (represented by arrow "U" in FIGS. 17 and 19). The hinge pin 1664 may be mounted within corresponding holes 1653 in the body segments 1652a, 1652b. See FIG. 22. As can also be seen in FIGS. 23 and 26-30, the distal end 1668 of the tissue plate 1660 has a downwardly protruding gear rack segment 1669 thereon that is adapted to drivingly interface with a gear assembly 1670.

As can be seen in FIGS. 22 and 23, gear assembly 1670 may include a first rack gear 1672 that is keyed onto a first gear shaft 1680 that is rotatably supported in holes 1682 in the body segments 1652a, 1652. A second step gear 1674 may also be keyed onto the first gear shaft 1680. The gear assembly 1670 may further include a third transfer gear 1676 that is keyed onto a second gear shaft 1690 that is rotatably supported in holes 1692 in the body segments 1652a, 1652b and in meshing engagement with the second step gear 1674. A fourth output gear 1678 is also keyed onto the second gear shaft 1690 and is in meshing engagement with a gear rack portion 1702 of an indicator member or base 1700 that is slidably supported in the carrier 216. Thus, as can be appreciated from reference to FIG. 27, as the tissue platform 1660 is depressed downward (arrow "DW"), the gear rack segment 1669 protruding therefrom causes the first rack gear 1672 to rotate counterclockwise "CCW" in FIG. 27 which also causes the second step gear 1674 to also rotate in the counterclockwise direction. The second step gear 1674 is in meshing engagement with the third transfer gear 1676 and is caused to rotate in the clockwise "CW" direction in FIG. 27. As the third transfer gear 1676 rotates clockwise, so does the output gear 1678. As the output gear 1678 rotates clockwise ("CW"), it drives the indicator base 1700 in the distal direction "DD" by virtue of its meshing engagement with the indicator rack 1702. In various embodiments, for example, a gear ratio of approximately 30 to 1 may be employed such that 60 mm of linear firing motion is accomplished in approximately 3 seconds. However, other gear ratios could conceivably be employed.

As can be most particularly seen in FIG. 23, the indicator base 1700 may be bifurcated into two lateral indicator leg portions 1710 that each terminate in an upstanding indicator plate 1712. Each indicator plate 1712 may have a series of thickness identifiers or indicators thereon. In particular, each indicator plate 1712, may have a first thickness identifier 1720 that corresponds to a first tissue thickness range "T1". For example, the first tissue thickness range "T1" may represent tissue having a thickness of about 0.75 mm to about 1.0 mm which would require a formed staple size of 0.75 mm. Each indicator plate 1712 may further have a second thickness identifier 1722 that corresponds to a second tissue thickness range "T2". For example, the second tissue thickness range "T2" may be for tissue having a thickness of greater than 1.0 mm to about 1.5 mm which would require a formed staple size of, for example, 1.0 mm. Each indicator plate 1712 may further have a third tissue thickness identifier 1724 that corresponds to a third tissue thickness range "T3" that corresponds to a third particular size of tissue. For example, the third thickness range "T3" may be for tissue having a thickness of greater than 1.5 mm to less than 2.0 mm which would require a formed staple size of, for example, 1.5 mm. Each indicator plate 1712 may further have a fourth tissue thickness identifier 1726 that corresponds to a fourth tissue thickness range "T4" that corresponds to a fourth particular size of tissue. For example, the fourth tissue thickness range "T4" may be for tissue having a thickness of about 2.0 mm which would require a formed staple size of, for example, 2.0 mm. The tissue identifiers 1720, 1722, 1724, 1726 may comprise, for example, numbers, letters, colors, etc. that are each understood to correspond to a particular tissue thickness range. In various embodiments, a proximal tissue stop 1721 may be provided on the cartridge 1652 to provide an abutment wall to position the tissue between the cartridge 1652 and the anvil assembly 20. See FIGS. 17, 22, and 24. Also in various embodiments, tissue grip members 1723 may be provided on the cartridge 1652 as shown in FIG. 22 to assist with the gripping and positioning of tissue between the cartridge 1652 and the anvil assembly 20.

As can be seen in FIG. 25, a view window 1730 may be provided in each lateral side portion of the housing 1610 to coincide with the tissue identifiers 1720, 1722, 1724, 1726 as will be discussed in further detail below. FIGS. 18 and 19 illustrate the positions of the indicator plates 1712 when no tissue has been clamped between the anvil assembly 20 and the tissue platform 1660. As can be seen in those Figures, none of the thickness indicators 1720, 1722, 1724, 1726 can be observed through the viewing windows 1730. FIGS. 26 and 27 illustrate the positions of the indicator plates 1712 when tissue having a tissue thickness range T1 is clamped between the anvil assembly 20 and the tissue platform 1660. As can be see in those Figures, the first tissue indicator 1720 is viewable through the corresponding window 1730.

Figure 30:
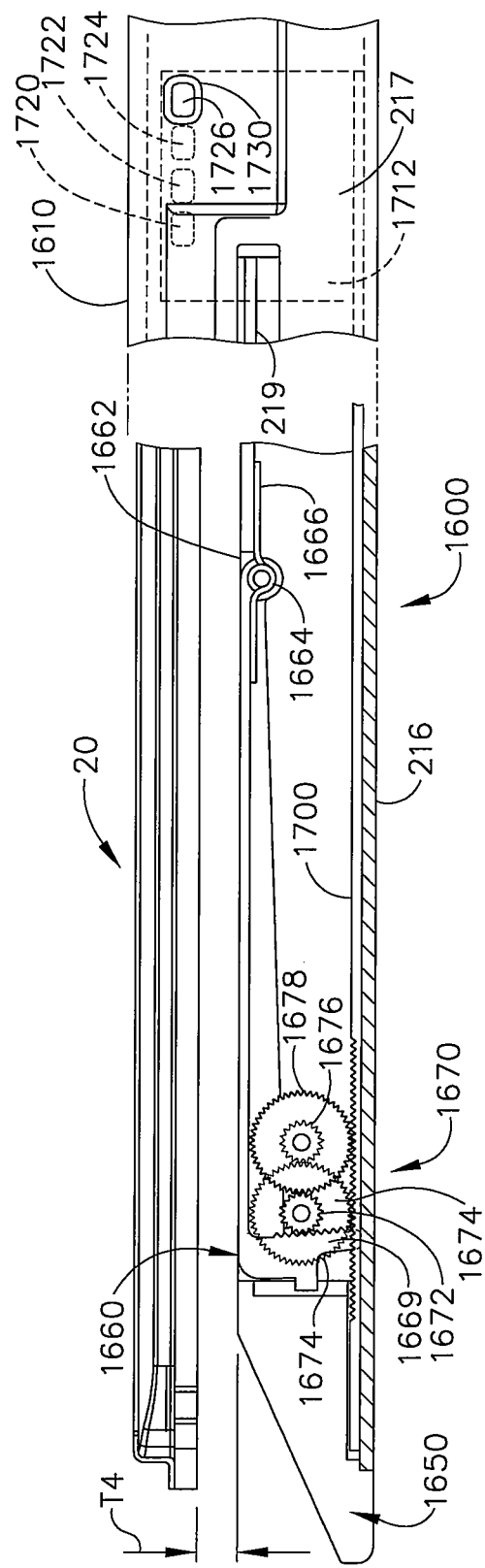
FIG. 30 is a side elevational view of the surgical tool embodiment of FIGS. 15-29 with the anvil assembly in a closed position for clamping tissue having a fourth thickness range therein.
Figure 31:
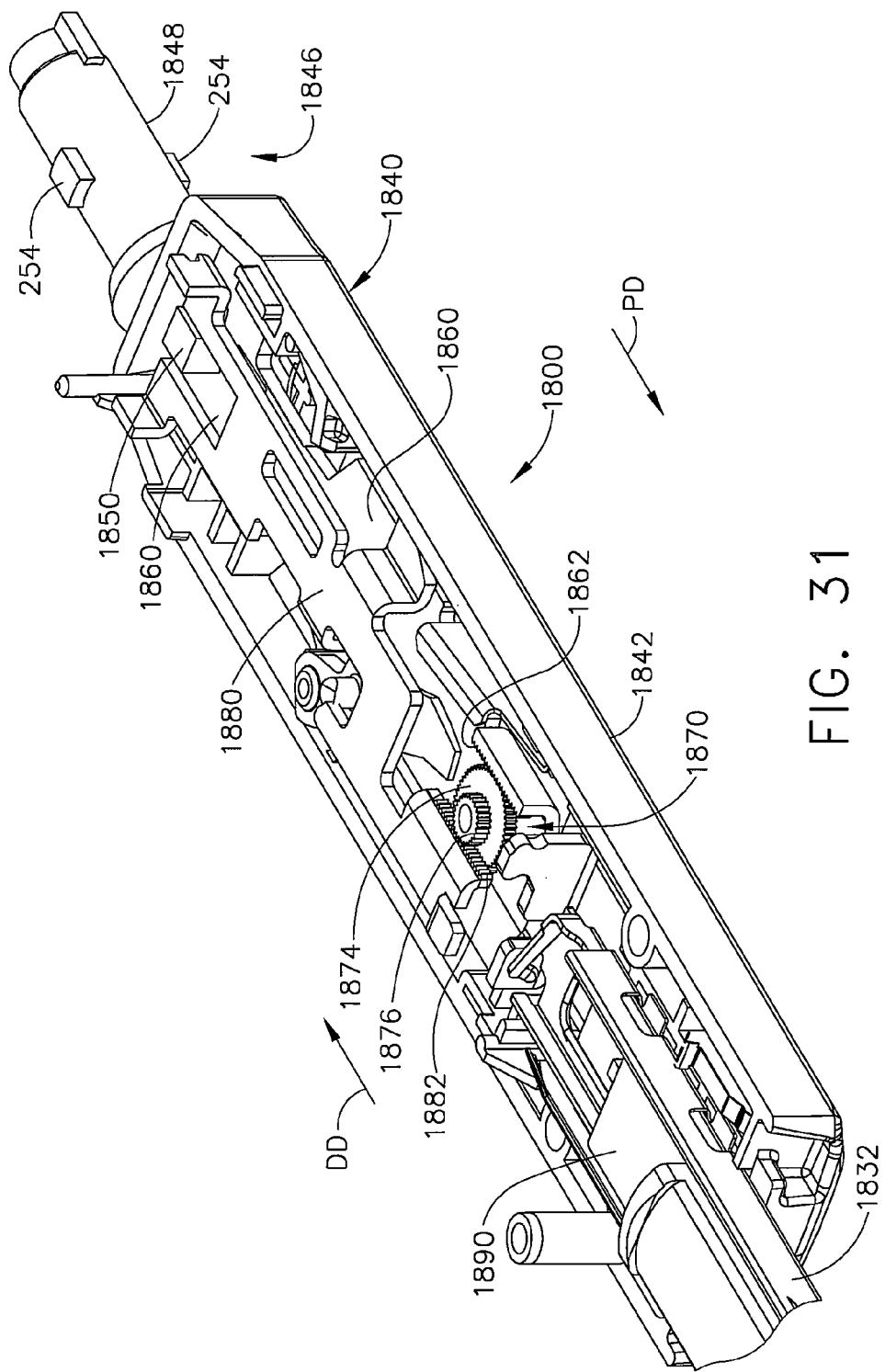
FIG. 31 is a perspective view of a portion of another surgical tool embodiment of the present invention with the cover removed therefrom.
Figure 32:
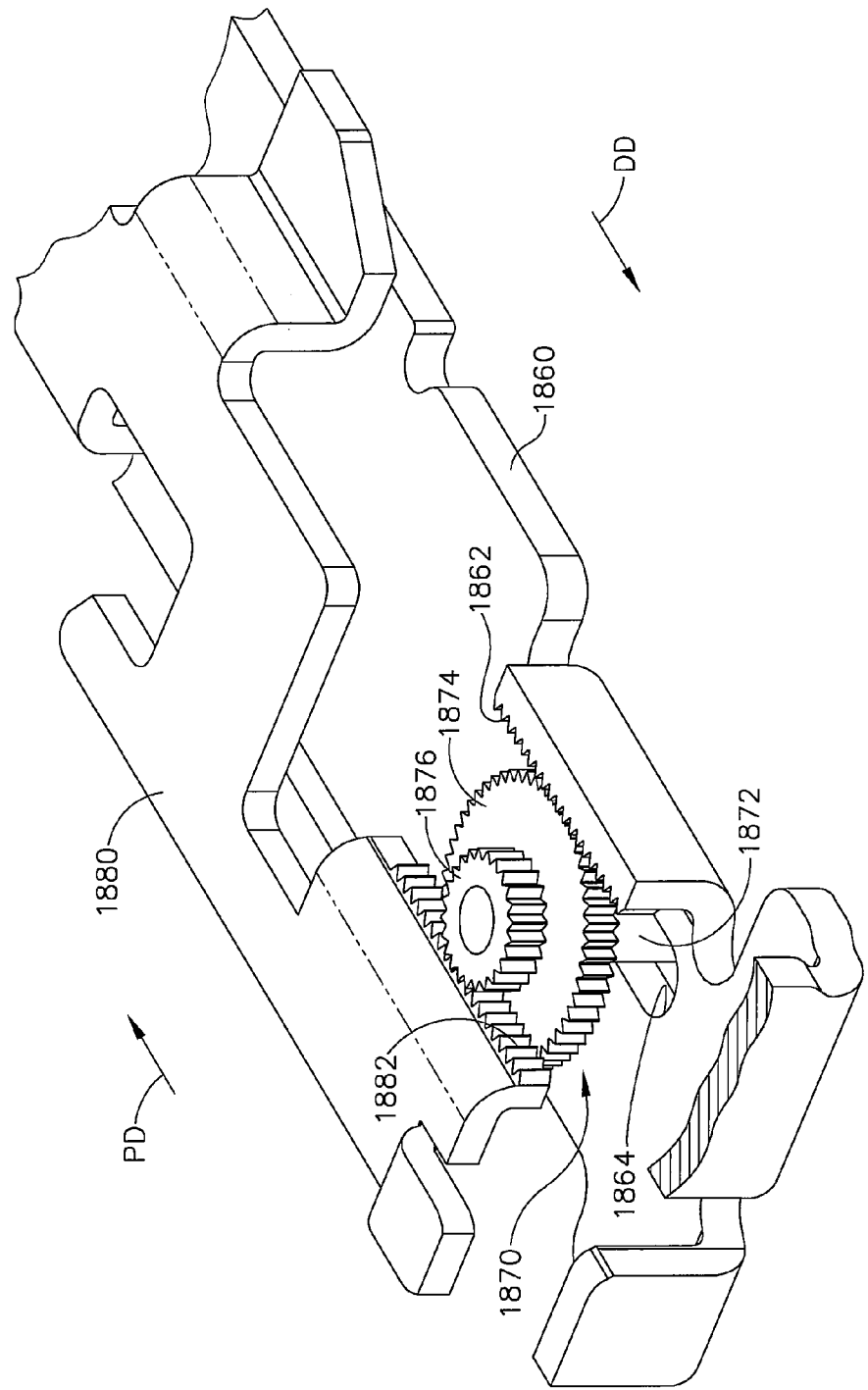
FIG. 32 is a perspective view of portions of a forming plate and feed plate arrangement of the surgical tool of FIG. 31.
Figure 33:
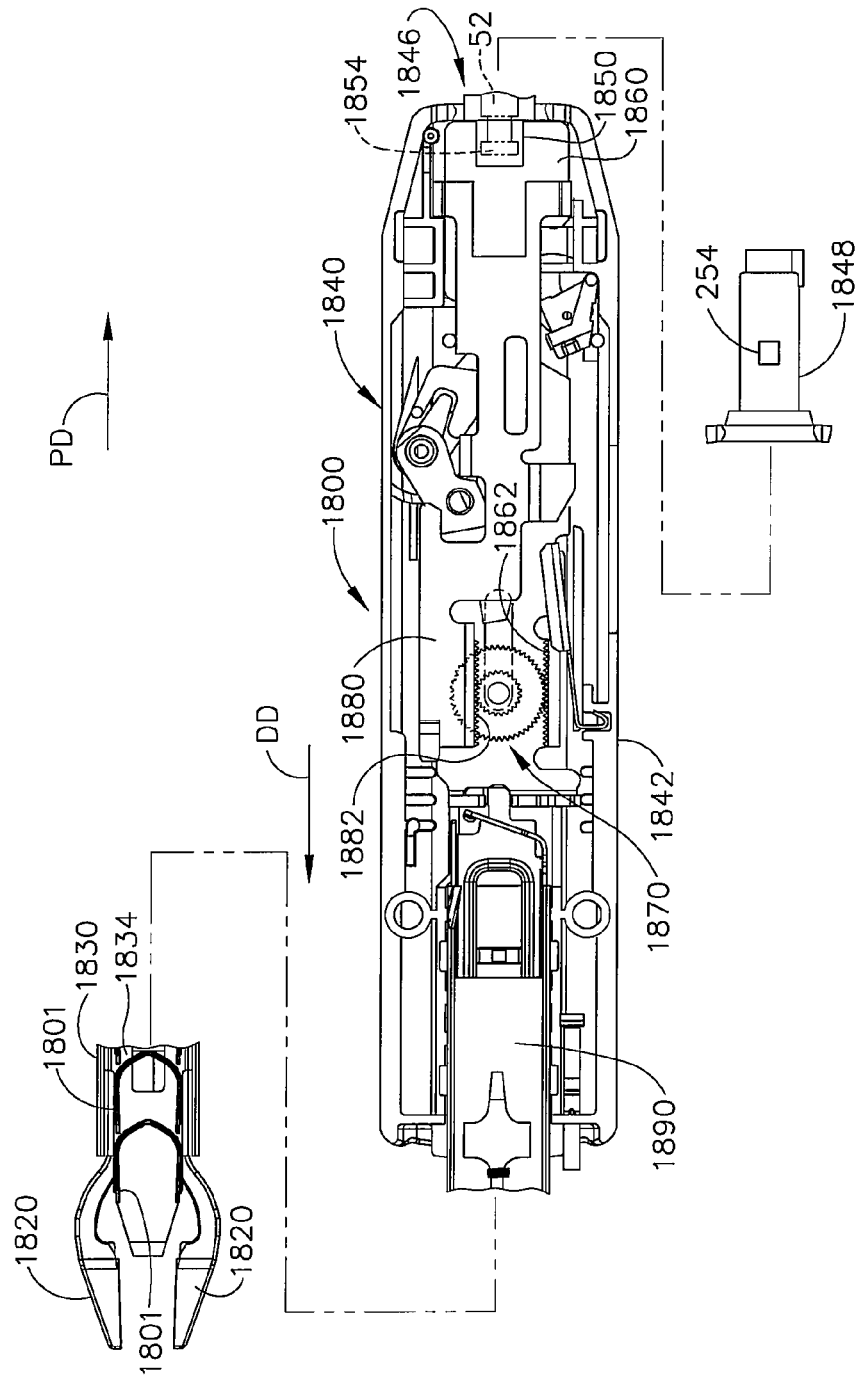
FIG. 33 is a plan view of the surgical tool embodiment of FIG. 31 with the cover removed for clarity.
Figure 34:
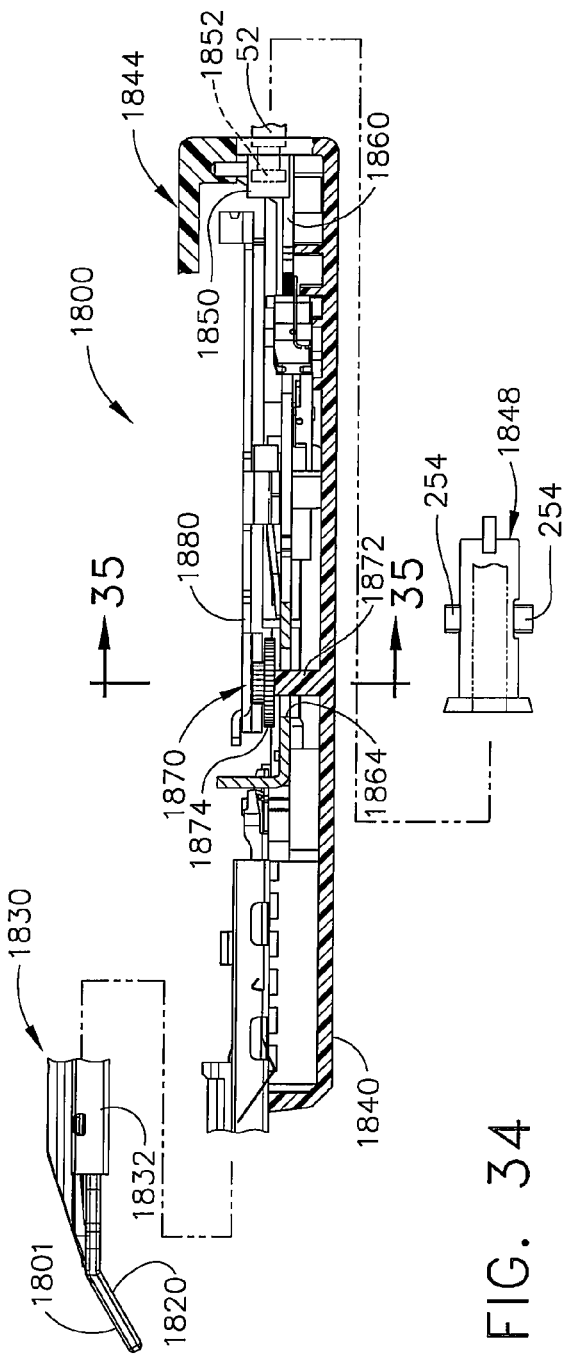
FIG. 34 is a cross-sectional view of the surgical tool of FIGS. 31-33.
Figure 35:
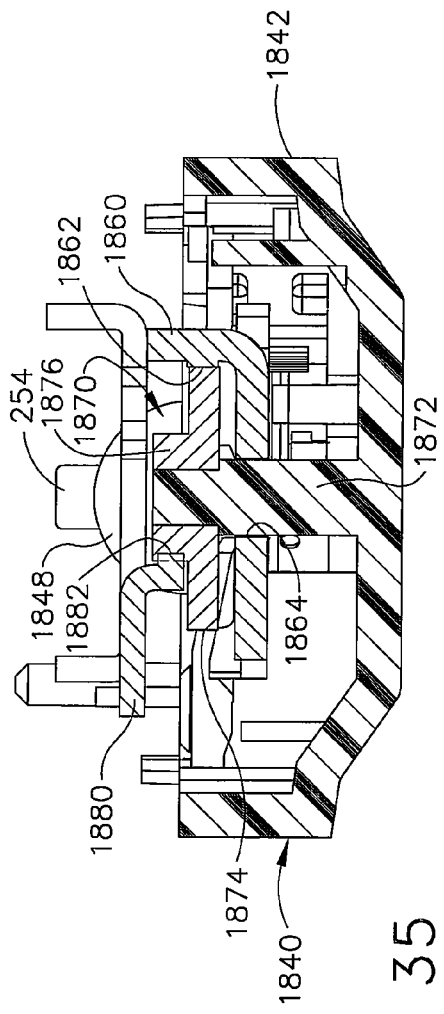
FIG. 35 is a cross-sectional view of the surgical tool of FIG. 34 taken along lines 35-35 in FIG. 34.

FIG. 28 illustrates the positions of the indicator plates 1712 when tissue having a tissue thickness range T2 is clamped between the anvil assembly 20 and the tissue platform 1660. As can be see in that Figure, the second tissue indicator 1722 is viewable through the corresponding window 1730. FIG. 29 illustrates the positions of the indicator plates 1712 when tissue having a tissue thickness range T3 is clamped between the anvil assembly 20 and the tissue platform 1660. As can be see in that Figure, the third tissue indicator 1724 is viewable through the corresponding window 1730. FIG. 30 illustrates the positions of the indicator plates 1712 when tissue having a tissue thickness range T4 is clamped between the anvil assembly 20 and the tissue platform 1660. As can be see in that Figure, the fourth tissue indicator 1726 is viewable through the corresponding window 1730. Thus, by operably attaching the surgical tool 1600 to the surgical instrument 10 and clamping a portion of target tissue to be stapled between the tissue platform 1660 and anvil assembly 20 (by activating the movable handle portion 24 toward the stationary handle portion 22), the clinician can ascertain the approximate thickness of the tissue to be stapled and then select a disposable stapling unit of for example, the type disclosed in U.S. Pat. No. 5,865,361 with the appropriate sized staples. The clinician then simply detaches the surgical tool 1600 from the surgical instrument 10 and then operably attaches the selected disposable stapling unit to the surgical instrument 10 and operates it as described in U.S. Pat. No. 5,865,361.

FIGS. 31-35 illustrate another surgical tool embodiment 1800 that comprises a clip applier for use with a surgical instrument 10 to apply at least one surgical clip 1801 to a human body. Various embodiments of the surgical tool 1800 may employ various components of the clip appliers disclosed in U.S. Pat. No. 5,951,574, the disclosure of which is herein incorporated by reference. The use of surgical clips 1801 to ligate structures within the body such as vessels, ducts, and tissue is well known in the surgical art. Various embodiments of the surgical tool 1800 may have a distal pair of opposed moveable jaws 1820 for receiving clips 1801 serially therein when the jaws 1820 are open and forming the clip 1801 received serially therein when the jaws 1820 are closed. See FIG. 33. The jaws 1820 may be connected to a distal end of a generally rectangular shaft 1830 that protrudes from a housing assembly 1840. The shaft 1830 may have a structural "U" shaped outer wrap 1832, a transparent upper shroud 1834, and a clip magazine containing a plurality of clips (not shown) located therein.

The housing assembly 1840 may include a base portion 1842 that has a cover 1844 attached thereto. See FIG. 34. The base portion 1842 has a proximal end 1846 that is configured for operable attachment to the elongated body 14 and the control rod 52 of the surgical instrument 10. The proximal end portion 1846 has a hollow connector portion 1848 that includes engagement nubs 254 for releasably engaging elongated body 14 of the surgical instrument 10.

The instrument 1800 may further include a firing rod connector 1850 that has a porthole 1852 therein for receiving the distal end 276 of the control rod 52. See FIG. 34. The firing rod connector 1850 is coupled to a forming plate 1860 that may be otherwise similar in construction to the forming mechanism 85 disclosed in U.S. Pat. No. 5,951,574, except for the differences discussed herein. As can be seen in FIGS. 31-33 and 35, the forming plate 1860 may have a forming rack 1862 thereon for meshing engagement with a gear assembly 1870. The gear assembly 1870 may be rotatably supported on a gear post 1872 that protrudes from the base portion 1842 and extends through an elongated slot 1864 in the forming plate 1860. The gear assembly 1870 may have a forming gear portion 1874 that is in meshing engagement with the forming rack 1862. The gear assembly 1870 may also comprise a feed gear 1876 that is attached to the forming gear 1874. The feed gear 1876 is in meshing engagement with a feed rack 1882 formed on a feed plate 1880 which performs the same functions as the feed mechanism 100 of U.S. Pat. No. 5,951,574. In various embodiments, the gear assembly 1870 and gear racks 1862, 1882 may have a 2:1 gear ratio, such that as the forming plate 1860 is driven in a distal direction "DD", the feed plate 1880 is simultaneously driven in the proximal direction "PD" only half as far as the forming plate 1860 was driven in the distal direction "DD".

The surgical tool 1800 also has a clip pusher 1890 (FIG. 33) that remains generally stationary throughout most of the simultaneous motion. The clip pusher 1890 is releasably coupled to the moving feed plate 1880 as the control rod 52 moves the feed plate 1880 in a proximal direction for the placement of a clip 1801 into the opening jaws 1820. The clip magazine within the shaft 1830 supplies additional clips 1801 to the feed plate 1880 and clip pusher 1890 for serial placement of the clips 1801 into the jaws 1802.

The surgical tool 1800 is activated by moving the control rod 52 in the distal direction "DD" which causes the closure of the jaws 1820 and the formation of each of the clips 1801 received serially therein. Moving the control rod 52 in the proximal direction "PD" opens the jaws 1820, releases the fully formed clip 1801, and feeds an unformed clip 1801 serially into the open jaws 1820. The surgical tool 1800 is coupled to the elongated body portion 14 and the control rod 52 in the manner described above and is operated by moving the movable handle portion 24 toward and away from the stationary handle portion 22 as was also described above. The person of ordinary skill in the art will understand that the surgical tool 1800 is especially adapted for use in open surgical applications thereby expanding the use of the conventional surgical instrument 10 which, in the past, has been limited to use in connection with endoscopic surgical procedures.

The tool assemblies of the prior disposable loading units that have been designed for use with the conventional surgical instrument 10 are configured to deploy staples in straight lines. During many surgical techniques, such as the resection of stomach tissue, for example, such a linear deployment is often preferred. During these techniques, the disposable loading unit is typically inserted through a cannula to access the surgical site and, as a result, it is often desirable for the tool assembly thereof to have a linear configuration that can be aligned with an axis of the cannula before the tool assembly is inserted therethrough. However, in some circumstances, those tool assemblies that have such a linear configuration are somewhat difficult to use. More particularly, for example, when the tool assembly must be placed adjacent to or against a cavity wall, such as the thoracic cavity wall, for example, it is often difficult for the surgeon to position a jaw of the tool assembly behind delicate or fragile tissue which is proximal to and/or attached to the cavity wall. Furthermore, even if the surgeon is successful in positioning a jaw behind the tissue, owing to the linear configuration of the tool assembly, the surgeon may not be able to see the distal end of the tool assembly. In some circumstances, surgical instruments that have a reusable blade and drive system have been developed to employ curved end effectors. Examples of such devices are disclosed in commonly owned U.S. patent application Ser. No. 11/652,170, filed Jan. 11, 2007 and entitled Surgical Stapler End Effector With a Tapered Distal End, the disclosure of which has been herein incorporated by reference.

Figure 36:
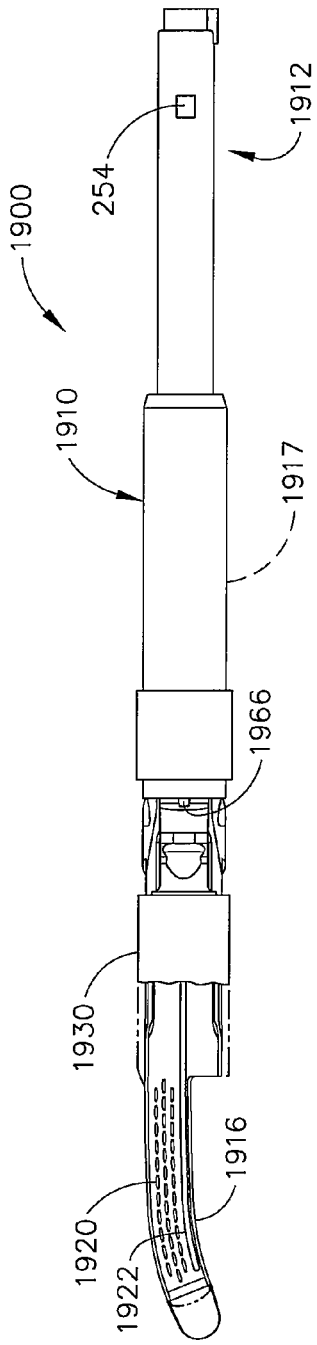
FIG. 36 is a plan view of another surgical tool embodiment of the present invention with a portion of the anvil assembly omitted for clarity.

FIG. 36 depicts another surgical tool embodiment 1900 of the present invention that may be used in connection with a surgical instrument 10. As can be seen in that Figure, the surgical tool 1900 may include a curved carrier 1916 that has a housing member 1910 attached thereto. The housing 1910 may be attached to the upstanding walls 1917 of the carrier portion by snap features or other suitable means. The housing member 1610 has a proximal end 1912 that is configured for removable attachment to the elongated body 14 of the surgical instrument 10. In particular, the proximal end 1912 may have engagement nubs 254 formed thereon which serve to form a bayonet-type coupling with the distal end of the elongated body portion 14 of the surgical instrument 10 as was described above.

Figure 37:
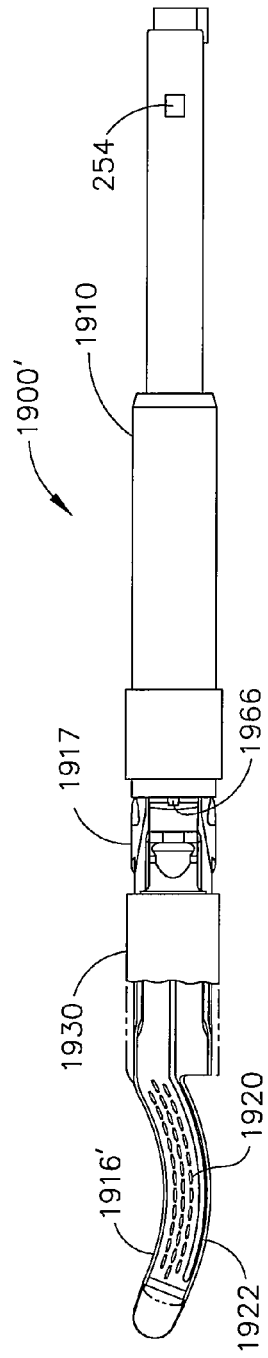
FIG. 37 is a plan view of another surgical tool embodiment of the present invention with a portion of the anvil assembly omitted for clarity.

In various embodiments of the present invention, the carrier 1916 and the staple cartridge 1920 supported therein are curved. In various embodiments, for example, the curvature of those components can be configured to substantially match the contour of a typical thoracic cavity wall. In these embodiments, the curvature of several thoracic cavity walls can be measured and statistically analyzed to determine the optimum profile of the curved end-effector. This profile can include several arcuate portions and, in addition, several linear portions. In other embodiments, the curvature of the thoracic cavity wall can be approximated by a single radius of curvature. Such embodiments can be simpler and less expensive to manufacture. In at least one embodiment, this radius of curvature is 1.2". In other various embodiments, the curvature of the carrier 1916 and staple cartridge 1920 can be configured to match the profile of the lower rectum, pelvis, or lower abdomen. FIG. 37 illustrates, for example, an alternative surgical instrument 1900' that employs a carrier 1916' that has a curvature that differs from the curvature of carrier 1916. Other curvatures disclosed in the aforementioned U.S. patent application Ser. No. 11/652,170 may also be employed.

In various embodiments of the present invention, the staple cartridge 1920 includes a curved slot 1922 for controlling the movement of axial drive assembly 1966 along a curved path. This curved slot 1922 can include several arcuate portions and several linear portions. In various embodiments, the curved slot 1922 can be defined by one radius of curvature. The anvil assembly 1930 which may otherwise be similar to the anvil assemblies described above, may have a curved portion (omitted for clarity in FIGS. 36 and 37) that substantially matches the curvature of the carrier 1916 and the staple cartridge 1920. In the embodiments illustrated in FIGS. 36 and 37, the staple cartridge 1920 has a curved slot 1922. The carrier 1916 and the anvil assembly may each have an identical slot (not shown) therein that, in connection with the slot 1922 are configured to receive a corresponding portion of a drive beam 1966 therein. The distal end of the drive member 1966 may be configured in the above described manner with respect to drive beam 266 to facilitate its driving activation by movement of the control rod 52 as described above. The proximal end of the drive beam 1966 containing the blade (not shown) may be configured such that, as the drive beam 1966 is driven in the distal direction "DD" by movement of the movable handle 24 of the surgical instrument 10, the drive beam 1966 tracks the curved path defined by the slot 1922.

Figure 38:
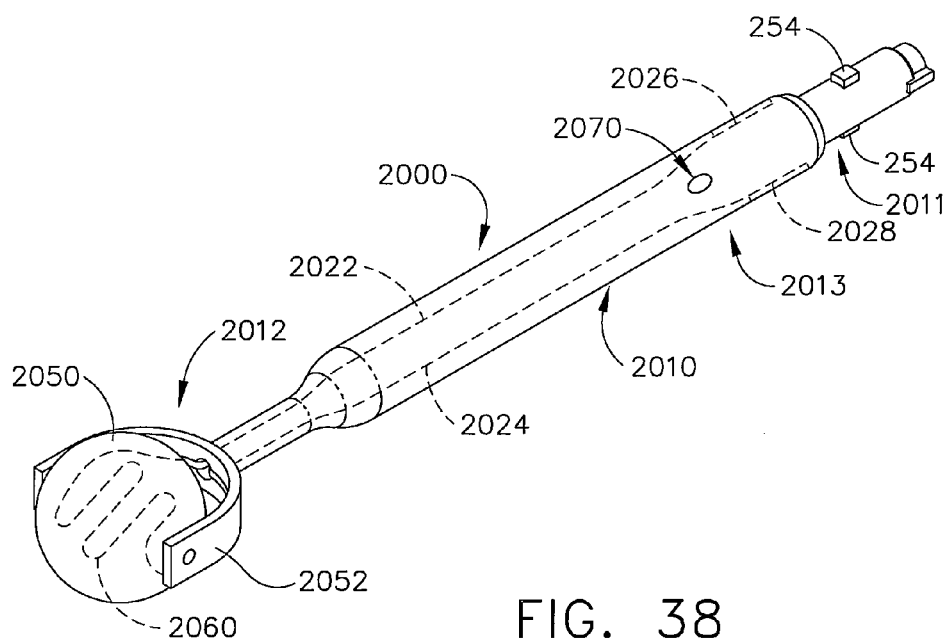
FIG. 38 is a perspective view of another surgical tool embodiment of the present invention.
Figure 39:
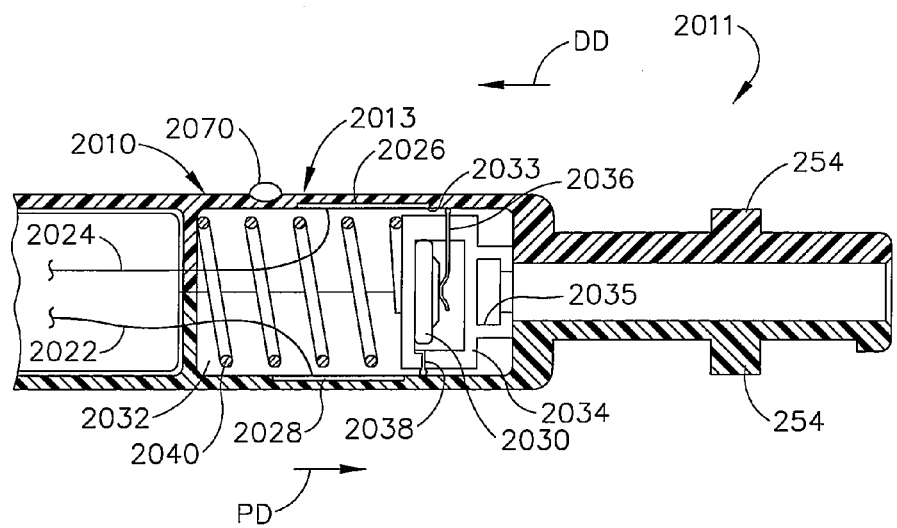
FIG. 39 is a cross-sectional view of a portion of the housing of the surgical tool of FIG. 38.

FIGS. 38 and 39 depict a surgical tool embodiment 2000 of the present invention that may be coupled to the surgical instrument 10 and used to cauterize tissue in an open surgical setting. As can be seen in those Figures, the surgical tool 2000 may include a housing 2010 that has a proximal end 2011 that is configured for removable attachment to the elongated body 14 of the surgical instrument 10. In particular, the proximal end 2011 may have engagement nubs 254 formed thereon which serve to form a bayonet-type coupling with the distal end of the elongated body portion 14 of the surgical instrument 10 as was described above.

The housing 2010 may further include a switch portion 2013 that movably houses a battery 2030 therein. The movable battery 2030 may be of the type and construction disclosed in commonly owned U.S. patent application Ser. No. 12/031,628, entitled Disposable Motor Driven Loading Unit For Use With a Surgical Cutting and Stapling Apparatus to Mark H. Ransick et al., now U.S. Pat. No. 7,793,812, that was filed on even date herewith and which is herein incorporated by reference. More specifically and with reference to FIG. 39, the switch portion 2013 of the housing 2010 defines a battery cavity 2032 that movably supports a battery holder 2034 that houses the battery 2030 therein. As can be seen in FIG. 39, a first battery contact 2036 is supported in electrical contact with the battery 2030 and protrudes out through the battery holder 2034 for sliding engagement with the inside wall 2033 of the battery cavity 2032. Similarly, a second battery contact 2038 is mounted in electrical contact with the battery 2030 and also protrudes out of the battery holder 2034 to slide along the inside wall 2033 of the battery cavity 2032. The battery holder 2034 has a control rod socket 2035 therein configured to receive the distal end 276 of control rod 52 when the proximal end 2011 of the surgical tool 2000 is coupled to the elongated body 14 of surgical stapling apparatus 10. As can also be seen in FIG. 39, a pair of contacts 2026, 2028 may be oriented within the wall 2033 for contact with the battery contacts 2036, 2038, respectively. The purpose of the contacts 2026, 2028 will be discussed in further detail below. As can also be seen in FIG. 39, a biasing member or switch spring 2040 is positioned within the battery cavity 2032 to bias the battery holder 2034 in the proximal direction "PD" such that when the surgical tool 2000 is not attached to the elongated body 14, the battery holder 2034 is biased to its proximal-most position shown in FIG. 39. When retained in that "pre-use" or "disconnected" position by spring 2040, the battery contacts 2036 and 2038 do not contact their respective contacts 2026, 2028 within the battery cavity 2032 to prevent the battery 2030 from being drained during non-use.

As can be seen in FIG. 38, the surgical tool 2000 may further include a non-staple applying end effector in the form of a ball-shaped end member 2050 that may be pivotally pinned to a yoke 2052 that is coupled to the distal end of the housing 2010. In various embodiments, the end effector 2050 may be fabricated from a conductive material such as stainless steel, titanium, etc. and have at least one electrically powered member 2060 therein. In the embodiment depicted in FIG. 38, the electrically powered member 2060 may comprise a heating element. Those of ordinary skill in the art will appreciate that the end-effector 2050 may be provided in a myriad of other shapes and configurations without departing from the spirit and scope of the present invention. As can be further seen in FIG. 38, the heating element 2060 may be electrically coupled to contacts 2026, 2028 by leads 2022, 2024, respectively.

Thus, when the surgical tool 2000 is unattached to the elongated body 14 of the surgical instrument 10, the battery 2030 will be biased into an unactuated position (FIG. 39) and therefore not be drained. In addition, attachment of the surgical tool 2000 to the elongated body 14 (and attachment of the control rod 52 to the battery holder socket 2035 will not result in the operation or draining of the battery 2030. To use the tool 2000, the clinician simply moves the movable handle 24 toward the stationary portion 22 of the handle assembly (FIG. 1) to drive the battery contacts 2036, 2038 into contact with contacts 2026, 2028, respectively which then powers the heating element 2060 in the end effector 2050. A light or other indicator 2070 may be supported by the housing 2010 and powered by the battery 2030 to provide the clinician with an indication that the heating element 2060 is being powered.

Figure 40:
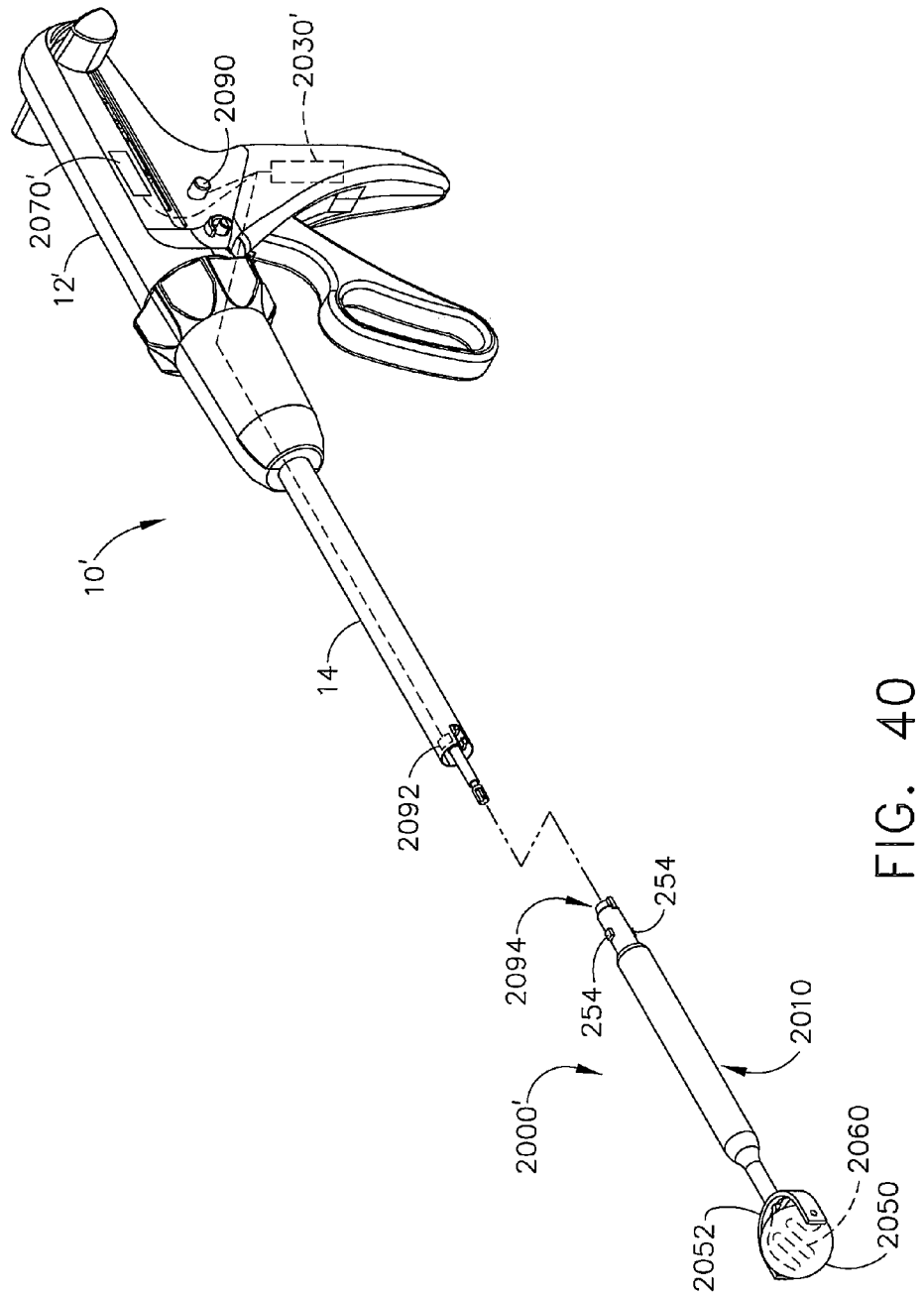
FIG. 40 is an exploded assembly view of another surgical tool embodiment of the present invention used in connection with another surgical instrument embodiment of the present invention.

FIG. 40 illustrates another surgical tool embodiment 2000' that is substantially similar to the surgical tool 2000 described above. However, in this embodiment, the surgical tool 2000' does not have a battery therein. The surgical tool 2000' is constructed for use with a surgical instrument 10' that has a battery 2030' that is operated by a switch 2090 that is mounted in the handle assembly 12'. The switch 2090 communicates with a contact assembly 2092 that is located in the distal end of the elongated body 14. The contact assembly 2092 is oriented to contact a contact 2094 mounted on the proximal end of the housing portion of tool 2000' when the tool 2000' is coupled to the elongated body 14. To activate the heating element 2060 in the end effector 2050, the clinician activates the button 2090 on the handle assembly 12'. A light 2070' may also be mounted on the handle assembly 12' to provide an indication of when the tool 2000' is being powered.

FIGS. 41 and 42 illustrate alternative housing embodiments 2200 and 2200' that may be used in place of the various housing arrangements described above when flexible drive assemblies are employed. In particular, these housings 2200, 2200' may at least be employed in connection with the various embodiments depicted in FIGS. 2-30 and 36-40 when drive assemblies that are capable of flexing or at least have portions that are capable of flexing are employed. The housing 2200 depicted in FIG. 41 may be configured as shown with a proximal end portion 2202 that is configured to receive the distal end of the control rod 52 therein and that has nubs 254 thereon to facilitate attachment to the elongated body 14 as was described above. In this embodiment, however, housing 2200 has a passive articulation joint member 2300 formed therein that facilitates passive articulation about the longitudinal axis L-L of the housing 2200 as shown. The passive articulation joint member 2300 may comprise a flexible conduit section 2302 that has interlocking ribs 2304 that are constructed to retain the passively articulated joint 2300 in an articulated orientation.

FIG. 42 illustrates another articulatable housing 2200' that has another passive articulation joint member 2300' that is coupled to a proximal housing portion 2400 by, for example, a proximal body collar 2310. The flexible articulation member 2300' has a body portion 2301 and include a plurality of kerfs 2302 separated by ribs 2304. In various embodiments, the kerfs 2303 and ribs 2304 may be equally spaced along the flexible articulation member 2300' thereby promoting a continuous bend radius when the flexible articulation member is articulated. A flexible articulation member 2300' having multiple bend radii may be achieved by providing unequal spacing between the kerfs 2303 and the ribs 2304. For example, such arrangement may be achieved by spacing the ribs 2304 more closely at one end and farther apart at the other end. As will be appreciated by those of ordinary skill in the art, increasing the spacing of the kerfs 2303 and/or the ribs 2304 reduces the bend radius of the section having increased spacing, more closely approximating a pivot point bend connection. Conversely spacing the kerfs 2303 and/or ribs 2304 more closely results in a more gradual bend, having a larger bend radius.

In the embodiment illustrated in FIG. 42, the kerfs 2302 comprise annular grooves that extend at least partially around the perimeter of the flexible articulation member 2300'. The kerfs 2302 preferably, however, comprise semi-annular grooves which are separated by a central longitudinal spine 2306 passing down the longitudinal axis L-L of the flexible articulation member 2300' such that a first plurality of ribs are formed on one lateral side of the spine 2306 and a second plurality of ribs 2304 are formed on another lateral side of the spine 2306. This spine 2306 assists in providing stiffening to the flexible articulation member 2300' and accommodates a slot (not shown) for receiving a drive assembly therethrough. The longitudinal spine 2306 may run the entire longitudinal length of the flexible articulation member 2300'. The flexible articulation member 2300' may also include a pair of side slot (not shown) passing through each rib 2304 on each lateral side for receiving a corresponding articulation plate (not shown) as discussed in commonly owned U.S. patent application Ser. No. 12/031,001, entitled Articulatable Loading Units For Surgical Stapling and Cutting Instrument to Frederick E. Shelton, IV et al., filed on even date herewith, the disclosure of which is herein incorporated by reference. As discussed therein, such articulation plates may be fabricated from a material that is relatively inelastic. That is, the plates may be fabricated from a material that retains its position after bending. Articulation plates may, for example, be fabricated from materials such as lead, copper, etc. Those of ordinary skill in the art will understand that at least a flexible or otherwise articulatable portion of a drive assembly supported within either of the housings 2300, 2300' is positioned to correspond with the flexible articulation member 2300, 2300' to facilitate articulation of the surgical tool without adversely affecting the operation of the drive assembly extending therethrough.

Thus, as will be appreciated by the foregoing, the various surgical tool embodiments of the present invention are especially suited for use with surgical instruments that were specifically designed for use in connection with disposable cutting and stapling units that have their dedicated cutting blade and are constructed to be disposed of after a single use. While such instruments may be commonly used in connection with multiple disposable cutting and stapling units, a clinician would have to have on hand several other dedicated instruments to perform other procedures during an operation. The interchangeable tool system of the present invention solves that problem. Thus, various embodiments of the present invention may comprise a surgical tool system that may include the surgical instrument 10 and at least two of the various surgical tools disclosed herein. For example, the surgical tools may comprise a manipulator 1000, nippers 1200, scissors 1300, a disposable endocutter 16, a tissue thickness measurement device 1600, staple appliers 1400, clip appliers 1800, cauterization devices 2000 and specimen retrieval devices 1100.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A disposable loading unit comprising:
   a housing configured to be coupled to a portion of a surgical instrument, said housing having a first lateral side and a second lateral side;

a carrier coupled to said housing;
an anvil movably supported for selective movement relative to said carrier in response to opening and closing motions from the surgical instrument to selectively move said anvil toward and away from said carrier;
a cartridge body configured to be removably received within said carrier;
a tissue measuring platform pivotally coupled to said cartridge body for movable travel relative thereto;
an indicator base movably supported by said cartridge body for axial travel relative thereto;
a gear assembly operably interfacing with said tissue measuring platform and said indicator base, such that movement of said tissue measuring platform causes said indicator base to move axially relative to said cartridge body; and
a plurality of thickness identifiers on said indicator base corresponding to particular tissue thicknesses and viewable from at least one location in said housing when tissue having said corresponding amount of tissue thickness is clamped between said anvil and said cartridge body.

2. The disposable loading unit of claim 1 wherein said indicator base comprises:
a first lateral indicator leg portion; and
a second lateral indicator leg portion and wherein a first group of said plurality of thickness identifiers are on a first indicator plate coupled to said first lateral leg portion and wherein another group of said plurality of thickness identifiers are on a second indicator plate coupled to said second lateral leg portion.

3. The disposable loading unit of claim 1 wherein a first group of said plurality of thickness indicators are viewable from said first lateral side of said housing and wherein a second group of said plurality of thickness indicators are viewable from said second lateral side of said housing.

4. The disposable loading unit of claim 1 wherein said plurality of thickness identifiers comprises:
a first thickness identifier corresponding to a first range of tissue thicknesses; and
a second thickness identifier corresponding to a second range of tissue thicknesses.

5. The disposable loading unit of claim 4 wherein said first range of tissue thicknesses comprises tissue thicknesses from 0.75 millimeters to 1.0 millimeters and wherein said second range of tissue thicknesses comprises tissue thicknesses from greater than 1.0 millimeters to 1.5 millimeters.

6. The disposable loading unit of claim 4 wherein said plurality of thickness identifiers further comprises a third tissue thickness identifier corresponding to a third range of thicknesses.

7. The disposable loading unit of claim 6 wherein said third range of tissue thicknesses comprises tissue thicknesses from greater than 1.5 millimeters to less than 2.0 millimeters.

8. The disposable loading unit of claim 6 wherein said plurality of thickness identifiers further comprises a fourth tissue thickness identifier corresponding to a fourth tissue thickness.

9. The disposable loading unit of claim 8 wherein said fourth tissue thickness comprises 2.0 millimeters.

10. The disposable loading unit of claim 1 wherein said plurality of thickness identifiers are selected from a group of thickness identifiers consisting of numbers, letters and colors.

11. The disposable loading unit of claim 1 wherein said plurality of thickness identifiers are viewable through at least one window in said housing.

12. The disposable loading unit of claim 1 wherein the surgical instrument comprises:
a handle assembly including a stationary portion and a movable portion; and
an elongated body protruding from the handle assembly and configured for removable attachment to the housing of the disposable loading unit, the elongated body interfacing with the movable portion of the handle assembly such that movement of the movable portion causes the elongated body to apply the opening and closing motions to the anvil.

13. The disposable loading unit of claim 1 further comprising tissue grip members on said cartridge body.

14. A surgical system comprising:
a surgical instrument comprising:
a handle assembly including a stationary portion and a movable portion; and
an elongated body protruding from the handle assembly and wherein said surgical system further comprises a plurality of disposable loading units comprising:
a disposable loading unit according to claim 1; and
at least one other disposable loading unit configured to cut and staple tissue.

15. A surgical method comprising:
providing a disposable loading unit according to claim 1;
removably coupling the disposable loading unit to an elongated body of a surgical instrument, the surgical instrument including a movable portion configured to generate the opening and closing motions for application to the disposable loading unit coupled to the elongated body;
positioning target tissue between the anvil and the tissue measuring platform of the disposable loading unit;
moving the movable portion of the surgical instrument to cause the anvil to compress the target tissue between the anvil and tissue measuring platform; and
viewing the plurality of thickness identifiers on the indicator base to determine a thickness of the target tissue.

16. The method of claim 15 further comprising:
releasing the target tissue from disposable loading unit;
detaching the disposable loading unit from the elongated body;
providing a plurality of other disposable loading units configured to cut and staple tissue wherein each other disposable loading unit has a plurality of staples corresponding to a particular thickness of tissue;
selecting one of the plurality of other disposable loading units that includes surgical staples that correspond to the target tissue thickness;
coupling the selected one of the other disposable loading units to the elongated body of the surgical instrument;
moving the movable portion of the surgical instrument to clamp the target tissue within the selected one of the other disposable loading units; and
actuating the surgical instrument to cause the selected other disposable loading unit to cut and staple the target tissue clamped therein.

* * * * *